United States Patent
Cantin et al.

(10) Patent No.: US 10,765,696 B2
(45) Date of Patent: Sep. 8, 2020

(54) COMPOSITIONS OF AND METHODS OF TREATMENT WITH ZWITTERIONIC POLYSACCHARIDE

(71) Applicants: City of Hope, Duarte, CA (US); California Institute of Technology, Pasadena, CA (US)

(72) Inventors: Edouard Cantin, Duarte, CA (US); Sarkis K. Mazmanian, Pasadena, CA (US); Chandran Ramakrishna, Duarte, CA (US)

(73) Assignees: CITY OF HOPE, Duarte, CA (US); California Institute of Technology, Pasadena, CA (US)

( * ) Notice: Subject to any disclaimer, the term of this patent is extended or adjusted under 35 U.S.C. 154(b) by 9 days.

(21) Appl. No.: 15/580,624

(22) PCT Filed: Jun. 10, 2016

(86) PCT No.: PCT/US2016/036803
§ 371 (c)(1),
(2) Date: Dec. 7, 2017

(87) PCT Pub. No.: WO2016/201169
PCT Pub. Date: Dec. 15, 2016

(65) Prior Publication Data
US 2018/0296587 A1 Oct. 18, 2018

Related U.S. Application Data

(60) Provisional application No. 62/173,423, filed on Jun. 10, 2015.

(51) Int. Cl.
| | | |
|---|---|---|
| *A61K 31/715* | (2006.01) | |
| *A61K 31/522* | (2006.01) | |
| *A61K 39/02* | (2006.01) | |
| *C08B 37/00* | (2006.01) | |
| *A61P 31/22* | (2006.01) | |
| *A61K 9/00* | (2006.01) | |

(52) U.S. Cl.
CPC .......... *A61K 31/715* (2013.01); *A61K 9/0053* (2013.01); *A61K 31/522* (2013.01); *A61K 39/02* (2013.01); *A61P 31/22* (2018.01); *C08B 37/006* (2013.01); *A61K 2300/00* (2013.01); *C12N 2710/16611* (2013.01); *Y02A 50/394* (2018.01); *Y02A 50/467* (2018.01)

(58) Field of Classification Search
CPC .. A61K 31/715; A61K 31/522; A61K 9/0053; A61K 39/02; A61P 31/22; C08B 37/006
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,679,654 A | 10/1997 | Tzianabos et al. |
| 2004/0219160 A1* | 11/2004 | Tzianabos ............ A61K 31/715 424/184.1 |
| 2007/0041986 A1 | 2/2007 | Blaszczak et al. |
| 2010/0226932 A1 | 9/2010 | Smith et al. |
| 2012/0309955 A1 | 12/2012 | Kasper et al. |

OTHER PUBLICATIONS

Lund et al., Science, 2008, 320(5880), p. 1220-1224. (Year: 2008).*
Emmert, D.H., Am Fam Physician., 2000, 61(6), p. 1697-1704, accessed online at https://www.aafp.org/afp/2000/0315/p1697.html. (Year: 2000).*
Kalka-Moll W.M. et al. (Apr. 2001). "Immunochemical and biological characterization of three capsular polysaccharides from a single Bacteroides fragilis strain," *Infect Immun* 69(4):2339-2344.
Pantosti, A. et al. (Jun. 1991). "Immunochemical characterization of two surface polysaccharides of Bacteroides fragilis," *Infect Immun* 59(6):2075-2082.
Ramakrishna, C. et al. (Jun. 2011, e-published Jun. 2, 2011). "Passively administered pooled human immunoglobulins exert IL-10 dependent anti-inflammatory effects that protect against fatal HSV encephalitis," *PLoS Pathogen* 7(6):e1002071.
Ramakrishna, C. et al. (Mar. 2013). "The case for immunomodulatory approaches in treating HSV encephalitis," *Future Virol* 8(3):259-272.
Wang Y. et al. (Dec. 5, 2000). "Structural basis of the abscess-modulating polysaccharide A2 from Bacteroides fragilis," *Proc. Natl. Acad. Sci. U.S.A.* 97(25):13478-13483.
International Search Report dated Aug. 30, 2016, for PCT Application No. PCT/US2016/036803, filed Jun. 10, 2016, 3 pages.
Written Opinion dated Aug. 30, 2016, for PCT Application No. PCT/US2016/036803, filed Jun. 10, 2016, 8 pages.

* cited by examiner

*Primary Examiner* — Jonathan S Lau
(74) *Attorney, Agent, or Firm* — Mintz, Levin, Cohn, Ferris, Glovsky and Popeo, P.C.

(57) ABSTRACT

The present disclosure includes compositions of a zwitterionic polysaccharide (e.g., *B. fragilis* capsular polysaccharide A (PSA)) (including active fragments thereof) and methods of treating viral infection and viral infection associated inflammation with compositions of a zwitterionic polysaccharide (e.g., *B. fragilis* capsular polysaccharide A (PSA)) (including active fragments thereof).

12 Claims, 23 Drawing Sheets

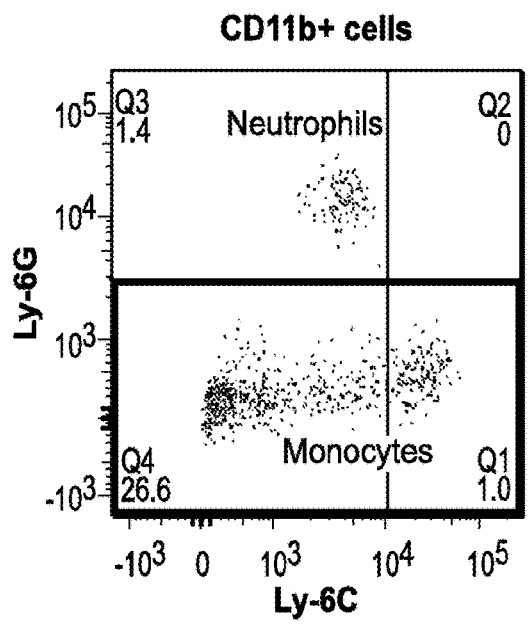
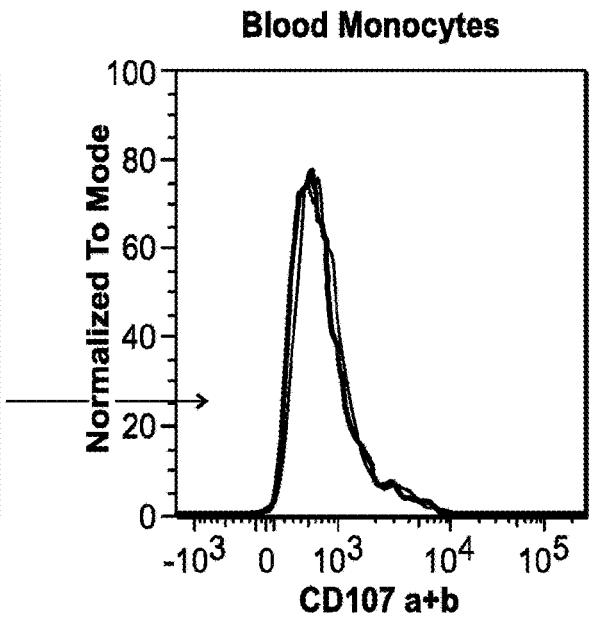
FIG. 4A
FIG. 4B
— Control
— HK-HSV Ag Stimulation
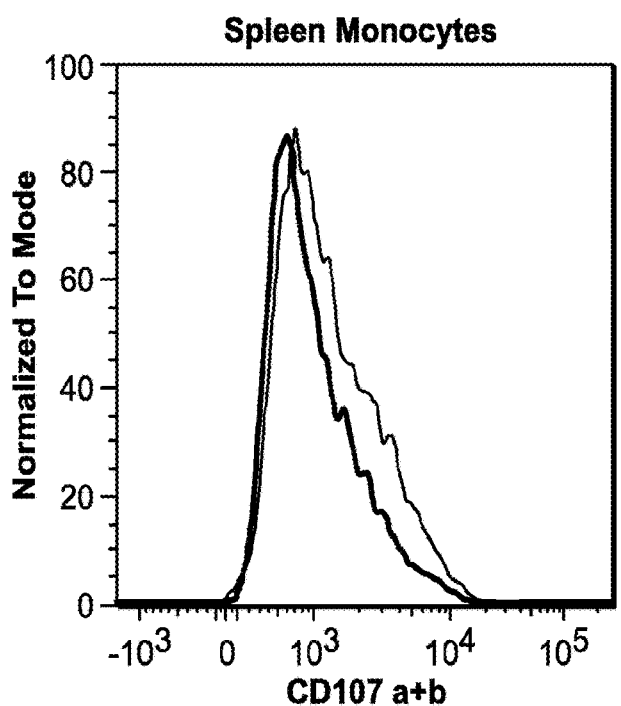
FIG. 4C

PSA

PBS

PSA

PBS

No Antigen Control

PMA + Ionomycin

HSV CD8 SSIEFARL peptide

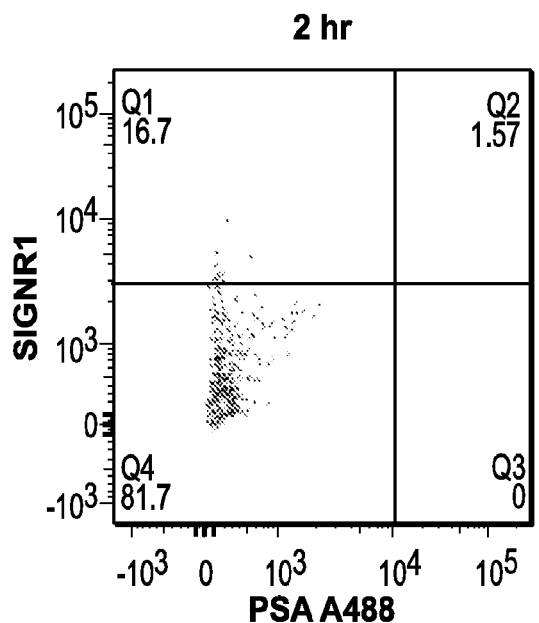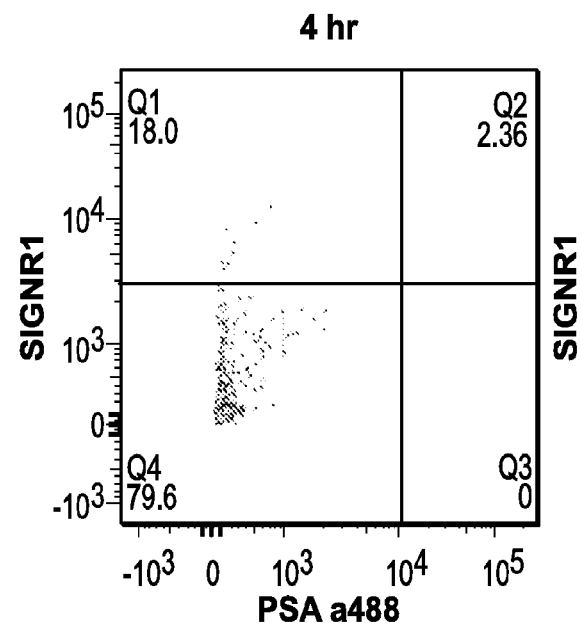
FIG. 13A          FIG. 13B
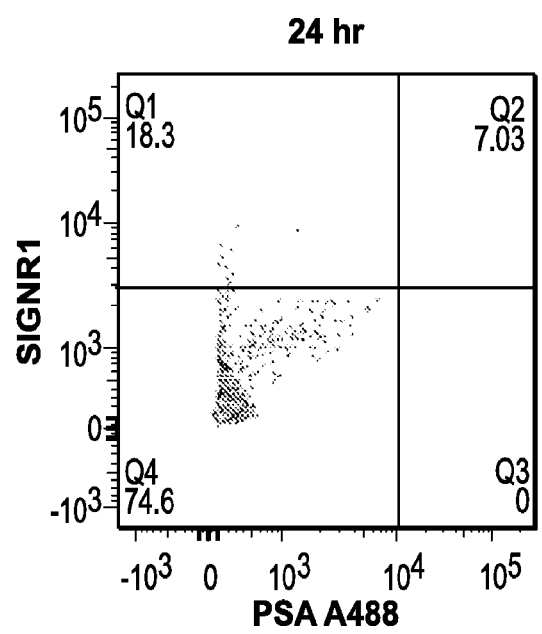
FIG. 13C

FIG. 16A
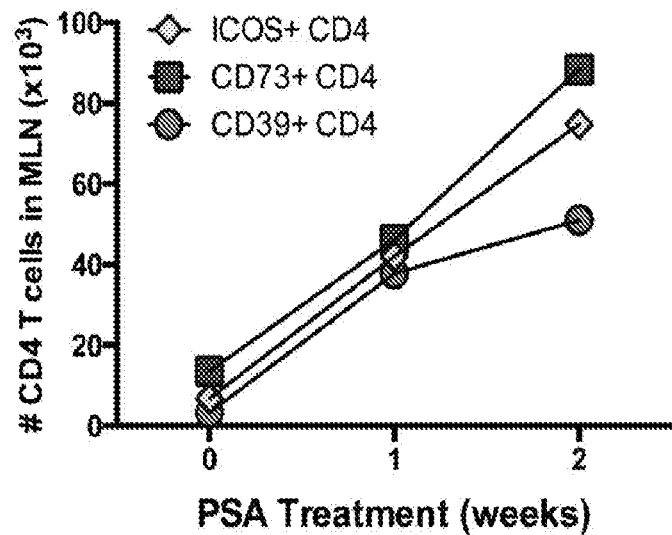
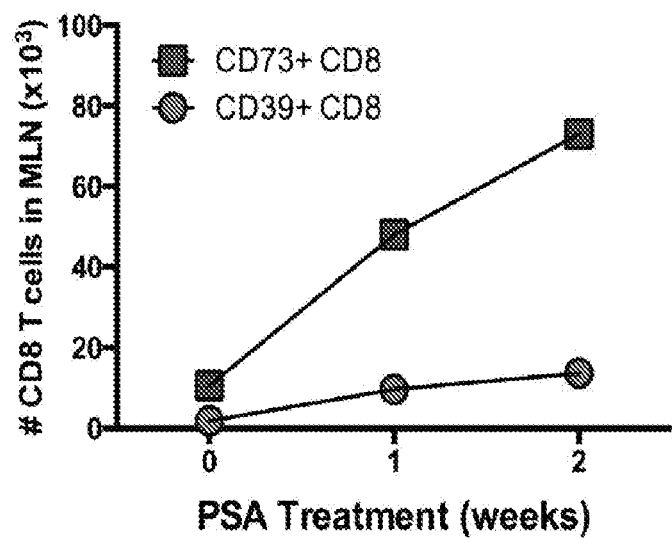
FIG. 16B

US 10,765,696 B2

COMPOSITIONS OF AND METHODS OF TREATMENT WITH ZWITTERIONIC POLYSACCHARIDE

CROSS-REFERENCE TO RELATED APPLICATIONS

This application is a Section 371 US national phase of PCT/US2016/036803 filed Jun. 10, 2016, which claims the benefit of priority under 35 U.S.C. § 119(e) to U.S. Application No. 62/173,423, filed Jun. 10, 2015, which is incorporated by reference herein in its entirety and for all purposes.

BACKGROUND OF THE DISCLOSURE

*Bacteroides fragilis* (*B. fragilis*) is a Gram-negative anaerobe and an integral component of the gut microflora of most mammals. Although members of the genus *Bacteroides* are numerically the most abundant intestinal organisms, *B. fragilis* itself represents only a very small fraction of the fecal flora in humans Although a minor component of the flora, *B. fragilis* is the most commonly isolated organism from clinical cases of intra-abdominal abscess. *B. fragilis* can produce at least eight structurally distinct capsular polysaccharides (denoted as polysaccharides A-H), of which polysaccharide A (PSA) is the most abundantly expressed.

There is a need for treating subjects with viral infection associated inflammation. Provided herein are compositions including PSA and methods of treating viral infection and viral infection associated inflammation with compositions including PSA.

BRIEF SUMMARY OF THE DISCLOSURE

The present disclosure includes, inter alia, pharmaceutical compositions including an effective amount of a zwitterionic polysaccharide (e.g., *Bacteroides fragilis* (*B. fragilis*) capsular polysaccharide A (PSA) or PSA2), and an anti-viral agent. The present disclosure includes, inter alia, a method of treating a viral infection in a subject, the method includes administering to the subject an effective amount of zwitterionic polysaccharide (e.g., *B. fragilis* capsular polysaccharide A (PSA)) (including active fragments thereof). The present disclosure includes, inter alia, a method of modulating an immune response in a subject, the method including administering to the subject an effective amount of a zwitterionic polysaccharide (e.g., *Bacteroides fragilis* (*B. fragilis*) polysaccharide A (PSA)) (including active fragments thereof), and an anti-viral agent. In embodiments, the methods of the present disclosure include administering a zwitterionic polysaccharide (e.g., PSA) and an anti-viral agent concurrently or sequentially.

In embodiments, the present disclosure includes a method of treating viral infection associated inflammation in a subject. The viral associated inflammation may be neuroinflammation. In embodiments, the present disclosure includes methods of treating neuroinflammation with a composition including a zwitterionic polysaccharide (e.g., PSA). In embodiments, the present disclosure includes compositions and methods for treating viral inflammatory diseases and for treating or moderating neurological sequelae in subjects with viral encephalitis.

Other features and advantages of the disclosure will be apparent from the following detailed description and claims.

Unless noted to the contrary, all publications, references, patents and/or patent applications reference herein are hereby incorporated by reference in their entirety for all purposes.

BRIEF DESCRIPTION OF THE DRAWINGS

FIG. 1A depicts 129S6 wild type (WT) mice infected by corneal scarification with a lethal dose of HSV and administered ACV at either 2, 3 or 4 days post-infection. FIG. 1B depicts a schematic of virus replication and $CD45^{high}$ inflammatory cell infiltration into the brainstem (BS) of 129 WT mice. FIG. 1C depicts virus titers in BS or trigeminal ganglia (Tg) of 129 WT mice infected with HSV, and given ACV or PBS for a week starting at day 4 post-infection. FIG. 1D depicts a survival graph of mouse survival following HSV infection of ACV or PBS treated groups. FIG. 1E are florescence activated cell sorting (FACS) plots indicating inflammation as measured by $CD45^{high}$ cell infiltration analyzed in the brainstem from control and ACV treated mouse.

FIG. 3A shows schedule of PSA dosage administered to 129 WT or Rag mice. FIG. 3B shows a survival plot of 129 WT or Rag mice (mice homozygous for the Rag1 mutation produce no mature T cells or B cells) that were given PSA as indicated in the schematic in FIG. 3A, prior to infection. FIG. 3C shows a bar plot of effects of PSA on CNS inflammation in Rag mice.

FIGS. 4A-4C depict florescence activated cell sorting (FACS) plots and normalized data showing that PSA suppresses spontaneous degranulation in monocytes. Monocytes (FIG. 4A) isolated from blood (FIG. 4B) and spleen (FIG. 4C) from PSA treated mice at day 6 post-infection are analyzed.

FIG. 5A shows BS cells analyzed for inflammatory $CD45^{high}$ cells at day 6 post infection in PSA and PBS treated mice. FIG. 5B depicts the percent $CD11b^+$ cells within BS $CD45^{high}$ infiltrating cells. FIG. 5C shows the percent inflammatory monocytes (IM) expressing high levels of Ly6C or CD107a/b within brainstem $CD45^{high}$ $CD11b^+$ monocytes. FIG. 5D shows the percent CD8 or CD4 T cells within $CD45^{high}$ infiltrating cells in the BS of PSA or PBS treated WT mice.

FIG. 6A depicts FACS plot depicting percent monocytes within infiltrating $CD45^{high}$ cells in BS of PBS treated group (right) and bar chart comparing total monocytes within BS $CD45^{high}$ infiltration cells in the 3 groups of mice (left). FIG. 6B depicts FACS plot depicting percent $Ly6C^{high}$ inflammatory monocytes within $CD45^{high}$ $CD11b^+$ monocyte population in the BS of PBS group (right) and a bar chart comparing $Ly6C^{high}$ monocytes within the BS of the 3 groups of mice. FIG. 6C depicts FACS plot depicting degranulation (CD107a/b) in monocytes (right) in the BS of PSA treated 129 WT mice, and a bar chart comparing the percent degranulating monocytes within the BS of the 3 groups (left).

FIGS. 8A-8B depicts FACS plots depicting CD4 T cells in blood and spleen of PSA treated mice. FIG. 8C shows a FACS plot from spleen of PBS treated mice. FIGS. 8D-8G depict FACS plots of CD4 T cells from cervical lymph nodes (CLN) (FIGS. 8D and 8F) and spleen (FIGS. 8E and 8G) isolated from 129 WT mice treated with either PSA or PBS by the oral route, and analyzed for CD25 and FoxP3 expression at day 6 post-infection.

FIGS. 13A-13D depict FACS of PSA+ SIGNR1+ Dendritic Cells (DCs) and polymorphonuclear leukocytes (PMNs) accumulate in the spleen over 24 hours following oral gavage. FIGS. 13A-13C depicts data for flow cytometric binding of PSA to DCs. FIG. 13D depicts histogram of neutrophils showing binding or phagocytosis of PSA binding cells at 24 hours in one mesentric lymph nodes (MLN).

FIG. 14A shows representative FACS plots of IFN-gamma and IL-10 secreting CD8 (left), CD4 (middle) and B cells (right) isolated from spleens of uninfected WT mice after 6 doses of oral PSA treatment. FIG. 14B shows bar plots depicting IL-10 secreting CD8 (left) and CD4 T cells (middle) and B cells (right) in the MLN and spleen of uninfected WT mice after 6 doses of oral PSA or PBS treatment.

FIG. 15A shows that cells from the draining cervical lymph nodes (CLN) of PSA (left) or PBS (right) treated HSV infected WT mice treated with ACV from d4 were analyzed at day 6 pi for FoxP3+ CD4 Tregs. FIG. 15B shows that CD4 gated cells in CLN were analyzed for CD25 expressing FoxP3+ Tregs. FIG. 15C shows that CD4 gated cells in CLN were analyzed for CD103+ FoxP3+ Tregs.

FIGS. 16A-16B depict line plots showing CD39, CD73 and ICOS surface expression on CD4 and CD8 T cells isolated from mesenteric LN (MLN) of uninfected WT mice at indicated times during oral PSA treatment. FIG. 16A depicts CD4 T cells isolated from MLN of uninfected WT mice at indicated times during oral PSA treatment. FIG. 16B depicts CD8 T cells isolated from MLN of uninfected WT mice at indicated times during oral PSA treatment.

FIG. 17A shows binding of oral fluorescent tagged PSA to CD45+ (boxed) intra-epithelial lymphocytes (left) isolated from ileum of treated 129 WT mice and Rag mice (middle); Middle plot gated on boxed CD45+ IEL cells in left plot. WT CD45+ cells binding PSA (Gated on PSA binding WT CD45+ IEL shown in box in middle plot) were mainly CD138+ B220+ plasmablasts (PB) and PDCA1+ B220+ CD11c+ plasmacytoid DCs (pDC); CD138+ B220$^{low}$ plasma cells (PC), B cells and other immune cells showed minimal binding (right plot). FIG. 17B shows IL-17 (left plot) and IL-10 secretion (right plot) from PSA stimulated CD45+ IEL (shown in box in left plot in FIG. A) isolated from ileum of 129 WT or Rag mice.

DETAILED DESCRIPTION OF THE DISCLOSURE

Figure 1A:
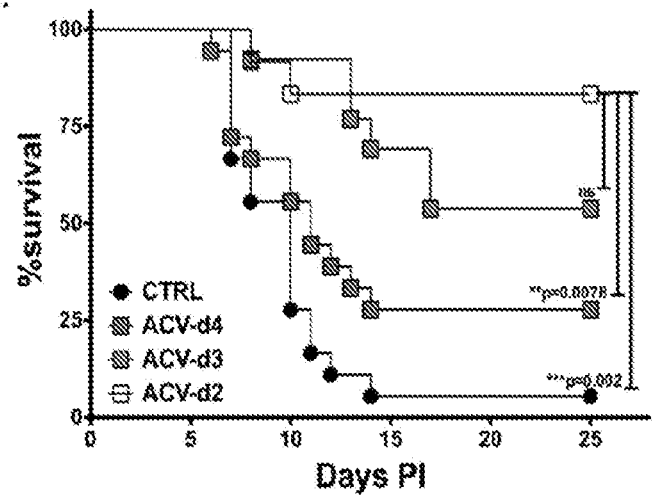
FIGS. 1A-1E are bar graphs of virus titers, survival and brainstem inflammation analysis.
Figure 1B:
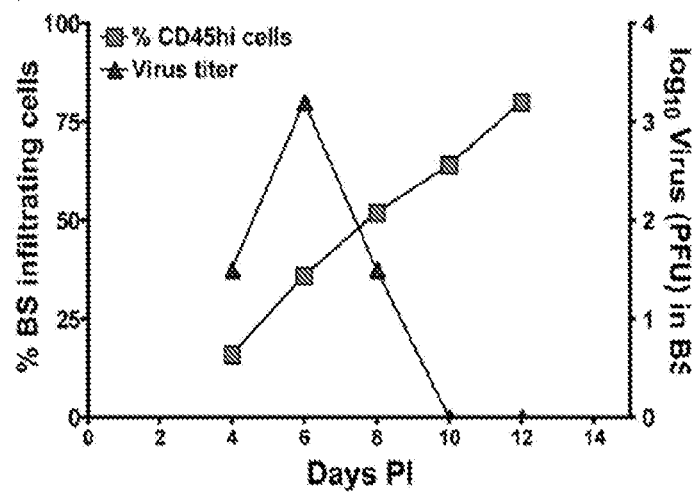
Figure 1C:
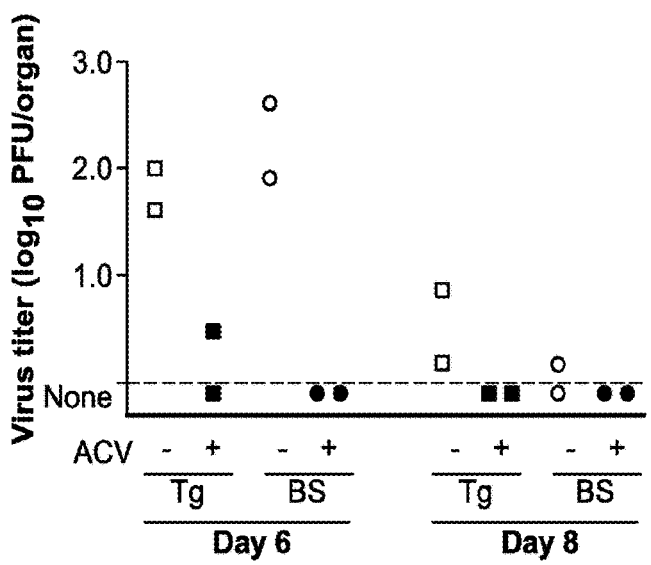
Figure 1D:
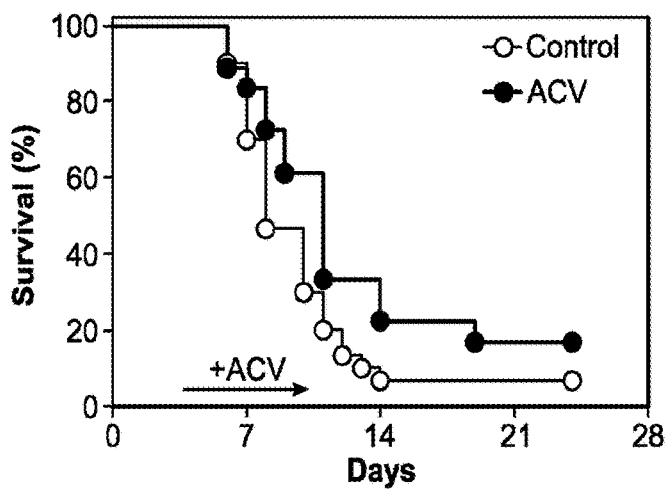
Figure 1E:
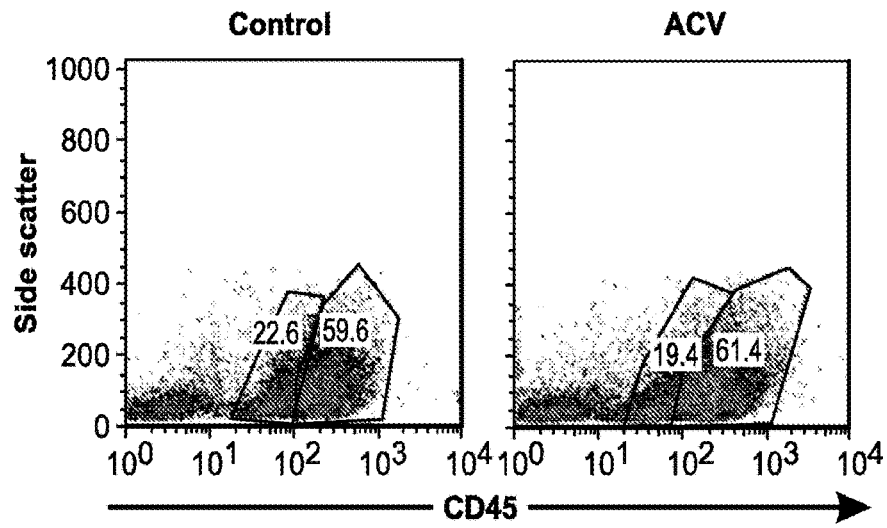

Provided herein are, inter alia, compositions and methods for treating viral infection, viral infection associated inflammation, and modulating immune response in a subject in need thereof.

The following definitions are included for the purpose of understanding the present subject matter and for constructing the appended patent claims. Abbreviations used herein have their conventional meaning within the chemical and biological arts.

Definitions

The term "zwitterionic polysaccharide or ZP" as used herein (i.e., in the present disclosure) refers to synthetic or natural polymers including one or more monosaccharides joined together by glycosidic bonds, and including at least one positively charged moiety and at least one negatively charged moiety. Zwitterionic polysaccharides include but are not limited to polymers of any length, from a mono- or di-saccharide polymer to polymers including hundreds or thousands of monosaccharides. In embodiments, a zwitterionic polysaccharide can include repeating units where each repeating unit includes from two to ten monosaccharides, a positively charged moiety (e.g., an free positively charged amino moiety) and a negatively charged moiety (such as sulfonate, sulfate, phosphate and phosphonate). In embodiment ZPs can have a molecular weight comprised between 500 Da and 2,000,000 Da. In embodiments, the ZPs can have a molecular weight between 200 and 2500. Exemplary ZPS include but are not limited to PSA and PSB from *Bacteroides Fragilis*, CP5/CD8 from *Staphylococcus aureus*, and Sp1/CP1 from *Streptococcus pneumonia*. Zwitterionic polysaccharides can be isolated from natural sources, and in particular from bacterial sources, e.g. by purification. Zwitterionic polysaccharides can also be produced by chemical or biochemical methods, as well as by recombinant microorganism technologies all identifiable by a skilled person.

In embodiments, as used herein *Bacteroides fragilis* (*B. fragilis*) capsular polysaccharide A (PSA) is used in accordance with its plain ordinary meaning in biology and refers to PSA as disclosed, for example in U.S. Pat. No. 5,679,654. This polysaccharide has a tetrasaccharide repeating unit containing one cationic free amine and one anionic carboxylate in each repeating unit. The natural occurring form of *B. fragilis* PSA contains several hundred repeating units of the tetrasaccharide. Free amino and carboxyl groups confer zwitterionic behavior to the PSA. PSA is also commonly known as PSA1. The *B. fragilis* PSA provided herein includes a sufficient numbers of the tetrasaccharide repeating unit to illicit, promote, or modulate an immune response or antiviral effect when administered according to the guidance provided herein into a subject.

The wording "polysaccharide A" as used herein indicates a molecule produced by the PSA locus of *Bacteroides Fragilis* and derivatives thereof which include but are not limited to polymers of the repeating unit {→3) α-d-AAT Galp(1→4)-[β-d-Galf(1→3)] α-d-GalpNAc(1→3)-[4,6-pyruvate]-β-d-Galp(1→}, where AATGal is acetamido-amino-2,4,6-trideoxygalactose, and the galactopyranosyl residue is modified by a pyruvate substituent spanning O-4 and O-6. The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining functional properties of the first polysaccharide. Accordingly, a derivative polysaccharide of PSA, usually differs from the original polysaccharide by modification of the repeating units or of the saccharidic component of one or more of the repeating units that might or might not be associated with an additional function not present in the original polysaccharide.

PSA2 as used herein refers to *B. fragilis* capsular polysaccharide as disclosed, for example in Wang Y. et al. (2000), *Proc. Natl. Acad. Sci. U.S.A.* 97:13478-83, and Kalka-Moll W M et al. (2001, *Infect Immun.*, 69:233944. *B. fragilis* PSA2 has a pentasaccharide repeating unit containing manoheptose, N-acetylmannosamine, 3-acetoamiod-3,6-dideoxyglucose, 2-amino-4-acetomido-2,4,6-trideoxygalactose, fucose, and 3-hydroxybutanoic acid. PSA2 is zwitterionic and carries one cationic free amine and one anionic carboxylate in each repeating unit.

The term "anti-viral agent" is used here in accordance with its plain ordinary meaning in Chemistry and Biology, and refers to a compounds (e.g. small molecule or a biologic) used for treating or preventing (e.g., prophylaxis) viral infection. The anti-viral agent can be a broad-spectrum anti-viral or be a specific anti-viral for treating or preventing a specific class or one viral infection. An anti-viral can also be an indirect anti-viral by promoting immune response in a subject.

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present disclosure, the methods disclosed herein are suitable for use in a patient that is a member of the Vertebrate class, Mammalia, including, without limitation, primates, livestock and domestic pets (e.g., a companion animal). Typically, a patient will be a human patient.

As used herein, "neuroinflammation" is inflammation of the nervous tissue. It may be initiated in response to a variety of cues, including infection, traumatic brain injury, toxic metabolites, or autoimmunity. Neuroinflammation can be chronic or acute. Chronic neuroinflammation is the sustained activation of glial cells and recruitment of other immune cells into the brain. Acute inflammation usually follows injury to the central nervous system immediately, and is characterized by inflammatory molecules, endothelial cell activation, platelet deposition, and tissue edema.

Neurotropic viruses are viruses that infect the central nervous system. Neurtropic viruses causing acute infection include Japanese, Venezuelan equine, and California encephalitis viruses, polio, coxsackie, echo, mumps, measles, influenza, and rabies viruses as well as members of the family Herpesviridae such as herpes simplex, varicella-zoster, cytomegalo and Epstein-Barr viruses. Those causing latent infection include herpes simplex and varicella-zoster viruses. Neurotropic viruses causing slow virus infection include measles, rubella and JC viruses, and retroviruses such as human T-lymphotropic virus 1 and human immunodeficiency virus. Prion, which is not a virus but a host-derived non-physiological protein, causes transmissible spongiform encephalopathy such as kuru and Creutzfeldt-Jakob disease that resemble slow virus infection.

"Microglial dysfunction" refers to abnormal function of the microglial cells, which are the resident immune cells of the central nervous system.

"Persistent viral infections" refer to viral infections in which the virus is not cleared but remains in specific cells of infected individuals. Persistent infections may involve stages of both silent and productive infection without rapidly killing or even producing excessive damage of the host cells. There are three types of overlapping persistent virus-host interaction that may be defined as latent, chronic and slow infection.

A "latent viral infection" is a type of persistent viral infection which is distinguished from a chronic viral infection. Latency is the phase in certain viruses' life cycles in which, after initial infection, proliferation of virus particles ceases. However, the viral genome is not fully eradicated. Latent viral infection is characterized by the lack of demonstrable infectious virus between episodes of recurrent disease.

Encephalitis is inflammation of the brain. Acute encephalitis associated with viral infections includes two distinct clinical-pathological diseases. The form referred to simply as acute viral encephalitis is direct infection of neural cells with perivascular inflammation, neuronal destruction, neuronophagia, and tissue necrosis, and this pathology is centered primarily in the gray matter. The other disease form, post-infectious encephalomyelitis (acute disseminated encephalomyelitis), is an illness that follows a variety of viral and some bacterial infections, with widespread perivenular inflammation and demyelination localized to the white matter of the brain. In addition to arboviruses and herpes simplex virus, many other viruses cause encephalitis that is milder, has fewer sequelae, and is associated with lower mortality rates.

Herpes simplex virus 1 (HSV-1) is a neurotropic α-herpesvirus that is associated with HSV encephalitis (HSE), which is the most prevalent sporadic viral encephalitis. Following primary infection at mucosal sites, the virus spreads rapidly via innervating sensory neurons to replicate in sensory ganglia and the CNS. Although infections in the nervous system are cleared rapidly in immunocompetent individuals, non-replicating viral genomes persist in latently infected neurons of sensory ganglia of the peripheral nervous system (PNS) and also in brainstem (BS) and brain neurons for the life of the host. Exposure to various stressors causes virus reactivation resulting in further spread and recurrent disease, most often including mucosal lesions and less frequently, but more seriously, diseases such as herpetic stromal keratitis and HSV encephalitis (HSE).

"Latent HSV viral infection" is used in accordance with its plain and ordinary meaning in virology. During acute herpes simplex virus (HSV) infection, virus and/or viral components (e.g., nucleocapsids) containing viral genetic material ascend in nerve axons from the initial site of infection to the sensory gangliamainly the trigeminal ganglia HSV-1, and the lumbar and sacral ganglia for HSV-2. In the sensory ganglia, the virus may cause a cytolytic infection or establish a latent, noncytolytic infection. Sympathetic ganglia and other cell types of the central nervous system may also serve as sites of virus latency. In the neuron, viral DNA is maintained as an extrachromosomal plasmid (episome) with 1 to 20 copies per cell. Transcription of LATs is regulated by LAT promoter elements. The LAT promoter region contains a series of consensus elements, including a TATA box, Sp1 binding motifs, cAMP response element and LAT promoter binding factor. Reactivation of latent infection and an associated down regulation of the LAT promoter, often occurs after various stress-related stimuli, e.g., heat, cold, ultraviolet light, unrelated immune hypersensitivity reactions, pituitary or adrenal hormones, immunosuppression, and emotional disturbance. When the latent virus is reactivated, its genome passes anterograde in axons to the epithelium, where productive replication takes place.

As used herein, the term "decrease" means lessening a condition from its initial or current state (e.g., quantitated as 100%) to less than 100% (e.g., 90%, 80%, 70%, 60%, 50%, 40%, 30%, 20% 10% or 1%).

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes all members of the animal kingdom prone to suffering from the indicated disorder. In some aspects, the subject is a mammal, and in some aspects, the subject is a human.

It must be noted that as used herein and in the appended embodiments, the singular forms "a," "an," and "the" include the plural reference unless the context clearly dictates otherwise.

As used herein, "treatment" is an approach for obtaining beneficial or desired results, including clinical results. For purposes of this disclosure, beneficial or desired clinical results include, but are not limited to, alleviation or amelioration of symptoms, diminishment of extent of disease, stabilized (i.e., not worsening) state of disease, preventing spread of disease, delay or slowing of disease progression, amelioration or palliation of the disease state, and recovery (whether partial or total), whether detectable or undetectable. "Treatment" can also mean prolonging survival as compared to expected survival if not receiving treatment.

By "reduce" or other forms of the word, such as "reducing" or "reduction," is meant lowering of an event or characteristic (e.g., HSV-1 encephalitis). It is understood that this is typically in relation to some standard or expected value, in other words it is relative, but that it is not always necessary for the standard or relative value to be referred to.

Insofar as the methods of the present disclosure are directed to preventing a disease or disease state, it is understood that the term "prevent" does not require that the disease state (e.g., HSV-1 encephalitis) be completely thwarted. The term "prevent" can encompass partial effects when the agents disclosed herein are administered as a prophylactic measure. The prophylactic measures include, without limitation, administration to one (or more) individual(s) who is suspected of being infected with, e.g., HSV-1, individuals who might be exposed to, e.g., HSV-1, and individuals already infected with, e.g., HSV-1 (whether they know it or not). The effects can extend from partial effect to differing degrees of effects, including an end effect of the individual being declared to be free of, e.g., HSV-1 infection. The term does not require that the disease state be completely avoided at all times.

As used herein, "palliating" a disease or disease state means that the extent and/or undesirable clinical manifestations of a disease state are lessened (or alleviated) and/or time course of the progression is slowed or lengthened, as compared to not treating the disease. Further, palliation does not necessarily occur by administration of one dose, but often occurs upon administration of a series of doses.

As used herein, "inhibiting," "inhibition," and its various noun and verbal permutations are used herein to describe the biological effects of the composition on, e.g., HSV-1. It does not necessarily require 100% inhibition. Partial inhibition is encompassed within this definition. Any degree of inhibiting as compared to the relevant control (e.g., a degree observed when the agent is not used) would be encompassed in the definition.

The term "modulate", "modulating" as used herein means regulating or adjusting to a certain degree.

The term "activate" and its various noun and verbal permutations as used herein means increasing expansion, differentiation, or functional stimulation of cells. For example, helper T cells are activated to become effector cells. The helper T cells are activated on the surface of antigen-presenting cells, which mature during the innate immune responses triggered by an infection. The innate responses also dictate what kind of effector cell a helper T cell will develop into and thereby determine the nature of the adaptive immune response elicited. To activate a cytotoxic or helper T cell to proliferate and differentiate into an effector cell, an antigen-presenting cell provides two kinds of signals. Signal 1 is provided by a foreign peptide bound to an MHC protein on the surface of the presenting cell. This peptide-MHC complex signals through the T cell receptor and its associated proteins. Signal 2 is provided by costimulatory proteins, especially the B7 proteins (CD80 and CD86), which are recognized by the co-receptor protein CD28 on the surface of the T cell. The expression of B7 proteins on an antigen-presenting cell is induced by pathogens during the innate response to an infection. Effector T cells act back to promote the expression of B7 proteins on antigen-presenting cells, creating a positive feedback loop that amplifies the T cell response. Signal 2 is thought to amplify the intracellular signaling process triggered by signal 1. If a T cell receives signal 1 without signal 2, it may undergo apoptosis or become altered so that it can no longer be activated, even if it later receives both signals. This is one mechanism by which a T cell can become tolerant to self-antigens. The combined actions of signal 1 and signal 2 stimulate the T cell to proliferate and begin to differentiate into an effector cell by a curiously indirect mechanism.

Monocytes express various receptors, which monitor and sense environmental changes. Monocytes are highly plastic and heterogeneous, and change their functional phenotype in response to environmental stimulation. Evidence from murine and human studies has suggested that monocytosis can be an indicator of various inflammatory diseases. Monocytes can differentiate into inflammatory or anti-inflammatory subsets. Upon tissue damage or infection, monocytes are rapidly recruited to the tissue, where they can differentiate into tissue macrophages or dendritic cells.

Throughout the description and claims of this specification the word "comprise" and other forms of the word, such as "comprising" and "comprises," means including but not limited to, and is not intended to exclude, for example, other components.

"Analog," "analogue," or "derivative" is used in accordance with its plain ordinary meaning within Chemistry and Biology and refers to a chemical agent that is structurally similar to another agent (i.e., a so-called "reference" agent) but differs in composition, e.g., in the replacement of one atom by an atom of a different element, or in the presence of a particular functional group, or the replacement of one functional group by another functional group, or the absolute stereochemistry of a chiral center of the reference agent.

In some embodiments, a derivative may be a conjugate with a pharmaceutically acceptable agent, for example, phosphate or phosphonate.

As used herein, the term "salt" refers to acid or base salts of the agents used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The therapeutic drugs can be administered alone or can be co-administered to the patient. Co-administration is meant to include simultaneous or sequential administration of the components individually or in combination. Thus, the preparations can also be combined, when desired, with other active substances. As used herein, "sequential administration" includes that the administration of two agents (e.g., the agents described herein) do not occur on a same day.

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, transdermal patches, etc.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997).

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

Pharmaceutical compositions may include compositions wherein the therapeutic drug (e.g., agents described herein, including embodiments or examples) is contained in a therapeutically effective amount, i.e., in an amount effective to achieve its intended purpose. The actual amount effective for a particular application will depend, inter alia, on the condition being treated.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

As used herein, "single-dosage form" means a unit dose or single dose packaged to contain a particular dose of the composition prescribed and/or administered to a patient. As used herein, "double-dosage form" means two unit doses of two different active agents packaged to contain respective doses of the agents prescribed and/or administered to a patient. "Double-dosage form" may include two agents as a single deliverable dosage unit or two agents separate dosage units.

For any therapeutic agent described herein, the therapeutically effective amount can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring agent's effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the agent. Thereafter, the dosage is increased by small increments until the optimum effect under circumstances is reached. Dosage amounts and intervals can be adjusted individually to provide levels of the administered agent effective for the particular clinical indication being treated. This will provide a therapeutic regimen that is commensurate with the severity of the individual's disease state.

The term "associated" or "associated with" in the context of a substance or substance activity or function associated with a disease means that the disease is caused by (in whole or in part) the substance or substance activity or function, a symptom of the disease is caused by (in whole or in part) the substance or substance activity or function, or a side-effect of the agent (e.g., toxicity) is caused by (in whole or in part) the substance or substance activity or function.

A weight percent of a component, unless specifically stated to the contrary, is based on the total weight of the formulation or composition in which the component is included.

"Excipient" is used herein to include any other agent that may be contained in or combined with a disclosed agent, in which the excipient is not a therapeutically or biologically active agent/agent. As such, an excipient should be pharmaceutically or biologically acceptable or relevant (for example, an excipient should generally be non-toxic to the individual). "Excipient" includes a single such agent and is also intended to include a plurality of excipients. For the purposes of the present disclosure the term "excipient" and "carrier" are used interchangeably throughout the description of the present disclosure and said terms are defined herein as, "ingredients which are used in the practice of formulating a safe and effective pharmaceutical composition."

The term "about" refers to any minimal alteration in the concentration or amount of an agent that does not change the efficacy of the agent in preparation of a formulation and in treatment of a disease or disorder (e.g., HSV-1 encephalitis). The term "about" with respect to concentration range of the agents (e.g., therapeutic/active agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Compositions

Provided herein, inter alia, are pharmaceutical compositions including an effective amount of a zwitterionic polysaccharide (e.g., *Bacteroides fragilis* (*B. fragilis*) capsular polysaccharide A (PSA)) and an anti-viral agent. The pharmaceutical compositions may additionally include a pharmaceutically acceptable excipient. *B. fragilis* has eight capsular polysaccharides, capsular polysaccharide A (PSA), capsular polysaccharide B (PSB), capsular polysaccharide C (PSC), capsular polysaccharide D (PSD), capsular polysaccharide E (PSE), capsular polysaccharide F (PSF), capsular polysaccharide G (PSG), capsular polysaccharide H (PSH). PSA is also known as PSA1. *Bacteroides fragilis* (*B. fragilis*) capsular polysaccharide A (PSA) is used in accordance with its plain ordinary meaning in biology and refers to PSA as disclosed, for example in U.S. Pat. No. 5,679,654 (contents of the patent with respect to the description of PSA is incorporated by reference herein in its entirety). This polysaccharide has a tetrasaccharide repeating unit containing one cationic free amine and one anionic carboxylate in each repeating unit. The natural occurring form of *B. fragilis* PSA contains several hundred repeating units of the tetrasaccharide. Free amino and carboxyl groups confer zwitterionic behavior to the PSA. PSA is also commonly known as PSA1. The *B. fragilis* PSA provided herein includes a sufficient number of the tetrasaccharide repeating units to illicit, promote, or modulate an immune response or antiviral effect when administered according to the guidance provided herein into a subject.

Zwitterionic polysaccharide useful according to the present disclosure include those naturally occurring polysaccharides or natural or non-natural derivatives thereof that include the requisite charged groups, and sufficient numbers of repeating units to illicit, promote, or modulate an immune response or antiviral effect when administered according to the guidance provided herein into a subject.

In embodiments, the present disclosure includes compositions of an effective amount of an active zwitterionic polysaccharide (e.g., PSA) fragment including a plurality (e.g. several) repeating units. In embodiments, an active zwitterionic polysaccharide (e.g., PSA) fragment may include 3 or more repeating units of the tetrasaccharide. In embodiments, an active zwitterionic polysaccharide (e.g., PSA) fragment may include 7-12, 12-17, or 15-22 repeating units of the zwitterionic polysaccharide (e.g., PSA) tetrasaccharide. In embodiments, the zwitterionic polysaccharide (e.g., PSA) active fragment includes one positive charge and one negative charge on each repeating unit. The positive charge may be in the form of a free amino group and the negative charge may be in the form of a carboxylate group, a phosphate group, phosphonate, sulfate, or a sulfonate group.

Bacteria used as the starting materials to obtain capsular polysaccharides can be obtained commercially from a number of sources. For example, the *B. fragilis*, NCTC 9342 and ATCC 23745 may be obtained from the National Collection of Type Cultures (London, England) and the American Type Culture Collection (Bethesda, Md.). Polysaccharide A can be purified from the above bacteria following standard protocol, e.g., the protocol described in Pantosti et al., *Infec. & Immun.,* 59:2075-2082 (1991). An example of the purification method is described in U.S. Pat. No. 5,679,654, contents of the method is incorporated by reference herein.

In embodiments, the present disclosure includes a pharmaceutical composition of an effective amount of a zwitterionic polysaccharide (e.g., capsular polysaccharide PSA) (including active fragments thereof), and an effective amount of an anti-viral agent, which may be, without limitation, aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivatives thereof, or any combination of such agents). In embodiments, an effective amount of capsular polysaccharide PSA is an amount effective to treat a viral infection in a subject in need thereof or to increase an immune response to a virus in a subject in need thereof. In embodiments, an effective amount of an anti-viral agent is an amount effective to treat a viral infection in a subject in need thereof in combination with an effective amount of a zwitterionic polysaccharide (e.g., capsular polysaccharide PSA). Thus, in such embodiments, an effective amount of the anti-viral agent and the effective amount of a zwitterionic polysaccharide (e.g., capsular polysaccharide PSA) are together a combined effective amount to treat a viral infection in the subject.

In embodiments, the present disclosure includes a pharmaceutical composition including an effective amount of a zwitterionic polysaccharide (e.g., *B. fragilis* capsular polysaccharide PSA) (including active fragments thereof), and an anti-viral agent in a single-dosage form. In embodiments, the present disclosure includes a pharmaceutical composition including an effective amount of a zwitterionic polysaccharide (e.g., *B. fragilis* capsular polysaccharide PSA) and an anti-viral agent in a double-dosage form. The pharmaceutical composition in a double-dosage form includes a first dosage form of a zwitterionic polysaccharide (e.g., *B. fragilis* capsular polysaccharide PSA) (including active fragments thereof), and a second dosage form of an anti-viral agent (e.g., aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivatives thereof, or any combination of such agents). In embodiments, the double dosage form may be a first oral dosage form of a zwitterionic polysaccharide (e.g., *B. fragilis* capsular polysaccharide PSA) (including active fragments thereof), and a second non-oral dosage form of an anti-viral agent. In embodiments, the double dosage form may be a first non-oral dosage form of a zwitterionic polysaccharide (e.g., *B. fragilis* capsular polysaccharide PSA) (including active fragments thereof), and a second oral dosage form of an anti-viral agent.

In embodiments, the present disclosure includes a pharmaceutical composition including an effective amount of a zwitterionic polysaccharide (e.g., *B. fragilis* capsular polysaccharide PSA) (including active fragments thereof), and an anti-viral agent in an oral dosage form. In embodiments, the present disclosure includes a pharmaceutical composition including an effective amount of a zwitterionic polysaccharide (e.g., *B. fragilis* capsular polysaccharide PSA) (including active fragments thereof), and an anti-viral agent in a single oral dosage form. In embodiments, the present disclosure includes a pharmaceutical composition including an effective amount of a zwitterionic polysaccharide (e.g., *B. fragilis* capsular polysaccharide PSA) (including active fragments thereof), and an anti-viral agent in a double oral dosage form. The pharmaceutical composition in a double oral dosage form includes a first oral dosage form of a zwitterionic polysaccharide (e.g., *B. fragilis* capsular polysaccharide PSA) (including active fragments thereof), and a second oral dosage form of an anti-viral agent (e.g., aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivatives thereof, or any combination of such agents).

In embodiments, the present disclosure includes administering to an individual, compositions of therapeutically effective amount of a zwitterionic polysaccharide (e.g., *B. fragilis* capsular polysaccharide PSA) (including active fragments thereof), alone or in combination with an anti-viral agent. The effective dose of the compositions may be between about 0.001 mg/kg to about 100 mg/kg of a zwitterionic polysaccharide (e.g., *B. fragilis* capsular polysaccharide PSA) (including active fragments thereof), e.g., the effective dose may be about 0.001 mg/kg, about 0.005 mg/kg, about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 25 mg/kg, about 30 mg/kg, about 40 mg/kg, about 50 mg/kg, about 60 mg/kg, about 70 mg/kg, about 75 mg/kg, about 80 mg/kg, about 90 mg/kg, or about 100 mg/kg. In embodiments, the compositions may have between about 0.1% to about 20% of the agent, e.g., the composition may have about 0.1%, about 0.5%, about 1%, about 5%, about 10%, about 15%, or about 20% of the agent. In embodiments, the compositions may include pharmaceutically acceptable diluent(s), excipient(s), and/or carrier(s).

The compositions including a zwitterionic polysaccharide (e.g., *B. fragilis* capsular polysaccharide PSA) (including active fragments thereof) may be administered with a suitable pharmaceutical carrier. The administration can be local or systemic, including oral, parenteral, intraperitoneal, intrathecal or topical application. The release profiles of such composition may be rapid release, immediate release, controlled release or sustained release. For example, the composition may comprise a sustained release matrix and a therapeutically effective amount. Alternatively, compositions including a zwitterionic polysaccharide (e.g., *B. fragilis* capsular polysaccharide PSA) (including active fragments thereof) can be secreted by genetically modified cells that are implanted, either free or in a capsule, at the gut of a subject. In embodiments, a composition including a zwitterionic polysaccharide (e.g., *B. fragilis* capsular polysaccharide PSA) (including active fragments thereof), may be administered to a subject via subcutaneous route. In embodiments, the composition may be administered as an oral nutritional supplement.

Oral compositions may include an inert diluent or an edible pharmaceutically acceptable carrier. They can be enclosed in gelatin capsules or compressed into tablets. For the purpose of oral administration, a zwitterionic polysaccharide (e.g., *B. fragilis* capsular polysaccharide PSA) can be incorporated with excipients and used in the form of tablets, troches, or capsules. Oral compositions can also be prepared using a fluid carrier for use as a mouthwash, wherein the agent in the fluid carrier is applied orally and swished and expectorated or swallowed. Pharmaceutically compatible binding agents or adjuvant materials can be included as part of the composition. The tablets, pills, capsules, troches and the like can contain any of the following ingredients, or agents of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

In embodiments, the compositions of a zwitterionic polysaccharide (e.g., *B. fragilis* capsular polysaccharide PSA) (including active fragments thereof), or a zwitterionic polysaccharide (e.g., *B. fragilis* capsular polysaccharide PSA) (including active fragments thereof), in combination with an anti-viral agent formulated for parenteral (including subcutaneous, intramuscular, and intravenous), inhalation, buccal, sublingual, nasal, rectal, topical, or oral administration for treating a viral infection, for inducing immune response, for treating neuroinflammation. The compositions may be conveniently presented in unit dosage form, and prepared by any of the methods well known to one skilled in the art.

In embodiments, the composition of the present disclosure may be formulated in dosage unit form for ease of administration and uniformity of dosage. Dosage unit form as used herein refers to physically discrete units suited as unitary dosages for the individual to be treated; each unit containing a predetermined quantity of agent calculated to produce the desired therapeutic effect in association with the required pharmaceutical carrier. The specification for the dosage unit forms are dictated by and directly dependent on the unique characteristics of the agent and the particular therapeutic effect to be achieved.

Method of Treating Viral Infections

Provided herein is a method of treating a viral infection in a subject in need thereof, the method includes administering to the subject an effective amount of a zwitterionic polysaccharide (e.g., *B. fragilis* capsular polysaccharide A (PSA)) (including active fragments thereof). In embodiments, the present disclosure includes a method of treating a viral infection in a subject in need thereof, including administering to the subject an effective amount of a zwitterionic polysaccharide (e.g., *B. fragilis* capsular polysaccharide A (PSA)) (including active fragments thereof), and an anti-viral agent. In embodiments, a zwitterionic polysaccharide (e.g., *B. fragilis* capsular polysaccharide A (PSA)) (including active fragments thereof) may decrease inflammation in a subject. The viral infection may be a DNA virus or an RNA virus infection.

In embodiments, the present disclosure includes administering to a subject an effective amount of PSA (including active fragments thereof), to treat herpesviruses including herpes simplex virus 1 (HSV-1) infection, HSV-2 infection, varicella-zoster virus (VZV) infection, cytomegalovirus (CMV) infection, Epstein-Barr virus (EBV) infection, Kaposi sarcoma associated herpesvirus (KHSV) infection, Human herpesvirus 6 (HHV6) infection, West-Nile virus infection, polyomaviruses infection, adenovirus infection, respiratory syncytial virus (RSV) infection, norovirus infection, or influenza virus infection.

In embodiments, the present disclosure includes administering to a subject an effective amount of a zwitterionic polysaccharide (e.g., *B. fragilis* capsular polysaccharide A (PSA)) (including active fragments thereof), to treat a viral infection associated inflammation, e.g., neuroinflammation. In embodiments, the neuroinflammation may be associated with a neurotropic virus infection in the subject. In embodiments, the neurotropic virus infection may be associated with neuronal or microglial dysfunction in the CNS of the subject. In embodiments, the virus infection may be arboviruses infection, influenza virus infection, herpesvirus infection, polyomavirus infection, or rotavirus infection. In embodiments, the present disclosure includes treating influenza pneumonia and HSV induced stromal keratitis.

In embodiments, the method of the present disclosure includes treating serious debilitating neurological sequelae in patients surviving HSE. In embodiments, the patients may also have CNS inflammation. In embodiments, the methods include combination treatment with ACV and PSA for preventing or moderating development of HSE and subsequent induction of long-term neurological complications.

In embodiments, the methods of the present disclosure include treating Herpes stromal keratitis (HSK), which is a leading cause of blindness. HSK is an inflammatory disease resulting from reactivated HSV infections that is usually treated with a combination of antivirals and corticosteroids. In embodiments, the methods of the present disclosure include treating HSK patients with a combination of PSA and an anti-viral.

In embodiments, the present disclosure includes a method of treating neuroinflammation in a subject in need with administering to the subject an effective amount of a zwitterionic polysaccharide (e.g., *B. fragilis* capsular polysaccharide A (PSA)) (including active fragments thereof). In embodiments, the neuroinflammation is HSV encephalitis, autoimmune encephalitis, coxsackievirus encephalitis, echovirus encephalitis, human immunodeficiency virus (HIV) encephalitis, adenovirus encephalitis, Epstein-Barr virus encephalitis, cytomegalovirus encephalitis, lymphocytic choriomeningitis virus (LCMV) encephalitis, arbovirus encephalitis, human herpesvirus 6 encephalitis, rabies virus encephalitis, vaccinia virus encephalitis, measles virus encephalitis, varicella-zoster virus encephalitis, mumps virus encephalitis, or influenza virus encephalitis.

In embodiments, the present disclosure includes a method for treating neuroinflammation in which a composition of a zwitterionic polysaccharide (e.g., *B. fragilis* capsular polysaccharide A (PSA)) (including active fragments thereof) is administered subsequent to, concurrently with, or before administering an anti-viral agent. In embodiments, the present disclosure includes a method of treating neuroinflammation in a subject in need, the method including administering to the subject a zwitterionic polysaccharide (e.g., *B. fragilis* capsular polysaccharide A (PSA)) (including active fragments thereof), and an anti-viral agent, for example, aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivatives thereof, or any combination of such agents.

In embodiments, the method of treating viral infection includes administering to a subject a composition including a zwitterionic polysaccharide (e.g., *B. fragilis* capsular polysaccharide A (PSA)) (including active fragments thereof), an anti-viral antibody. In embodiments, the antibody may be a humanized antibody. In embodiments, the antibody may be a humanized polyclonal or monoclonal antibody. The antibody may be a neutralizing monoclonal antibody against a viral surface antigen.

In embodiments, the method of treating viral infection includes administering to a subject a composition including a zwitterionic polysaccharide (e.g., *B. fragilis* capsular polysaccharide A (PSA)) to treat drug-resistant viral infection, e.g., drug-resistant HSV-1 or HSV-2 infection. In embodiments, the method includes treating drug resistant viral infection by administering a composition including a zwitterionic polysaccharide (e.g., *B. fragilis* capsular polysaccharide A (PSA)) and an anti-viral agent, e.g., a humanized anti-viral antibody.

Method of Modulating Immune Response

The present disclosure includes a method of modulating an immune response in a subject in need thereof, the method including administering to the subject an effective amount of a zwitterionic polysaccharide (e.g., *Bacteroides fragilis* (*B. fragilis*) polysaccharide A (PSA)) (including active fragments thereof), and an anti-viral agent. In embodiments, the method includes modulating immune response of patients who suffer frequent bouts of recurrent viral infection, e.g., HSV infection. In embodiments, a zwitterionic polysaccharide (e.g., *B. fragilis* capsular polysaccharide A (PSA)) (including active fragments thereof) may activate B cells. In embodiments, a zwitterionic polysaccharide (e.g., *B. fragilis* capsular polysaccharide A (PSA)) (including active fragments thereof) may activate immature B cells (e.g., CD138+ B cells, B220+ B cells, or CD138+ B220+ B cells), plasmablasts, and/or T cells (e.g., ICOS+ T cells, CD103+ T cells, CD4+ T cells, ICOS+CD4+ T cells,CD8+ T cells, CD103+ CD8+ T cells,CD4+ CD8+ T cells,CD45+ T cells, IEL T cells, and/or CD45+ IEL T cells). In embodiments, a zwitterionic polysaccharide (e.g., *B. fragilis* capsular polysaccharide A (PSA)) (including active fragments thereof) may increase regulatory T cells. In embodiments, a zwitterionic polysaccharide (e.g., *B. fragilis* capsular polysaccharide A (PSA)) (including active fragments thereof) may activate innate immune cells. In embodiments, a zwitterionic polysaccharide (e.g., *B. fragilis* capsular polysaccharide A (PSA)) (including active fragments thereof) may activate plasmacytoid dendritic cells. In embodiments, a zwitterionic polysaccharide (e.g., *B. fragilis* capsular polysaccharide A (PSA)) (including active fragments thereof) may decrease inflammatory monocytes (e.g., Ly6C inflammatory monocytes, CD107a/b inflammatory monocytes, and/or Ly6C CD107a/b inflammatory monocytes). In embodiments, the method of modulating an immune response in a subject in need thereof is a method of increasing an immune response to a virus in a subject in need thereof.

In embodiments, a zwitterionic polysaccharide (e.g., *B. fragilis* capsular polysaccharide A (PSA)) (including active fragments thereof) may decrease CD11b+ inflammatory monocytes. In embodiments, a zwitterionic polysaccharide (e.g., *B. fragilis* capsular polysaccharide A (PSA)) (including active fragments thereof) may decrease Ly6C CD11b+ inflammatory monocytes. In embodiments, a zwitterionic polysaccharide (e.g., *B. fragilis* capsular polysaccharide A (PSA)) (including active fragments thereof) may decrease $CD45^{high}$ inflammatory monocytes. In embodiments, a zwitterionic polysaccharide (e.g., *B. fragilis* capsular polysaccharide A (PSA)) (including active fragments thereof) may decrease $CD45^{high}$ CD11b+ inflammatory monocytes.

In embodiments, the subject for modulating immune response of this disclosure may have viral infection, for example, herpesviruses including herpes simplex virus 1 (HSV-1) infection, HSV-2 infection, varicella-zoster virus (VZV) infection, cytomegalovirus (CMV) infection, Epstein-Barr virus (EBV) infection, Kaposi sarcoma associated herpesvirus (KHSV) infection, Human herpesvirus 6 (HHV6) infection, west-nile virus infection, Polyomaviruses infection, Adenovirus infection, Respiratory syncytial virus (RSV) infection, norovirus infection, or influenza virus infection.

In embodiments, the subject for modulating immune response of this disclosure is administered a composition of a zwitterionic polysaccharide (e.g., *B. fragilis* capsular polysaccharide A (PSA)) (including active fragments thereof), subsequent to, concurrently with, or before administering an anti-viral agent, wherein the anti-viral agent is, for example, aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivatives thereof, or any combination of such agents.

Dosage and Regimens

In embodiments, one to six doses of a zwitterionic polysaccharide (e.g., *B. fragilis* capsular polysaccharide A (PSA)) are administered (e.g., IP) on 9 days before HSV infection, 6 days before HSV infection, 3 days before HSV infection, day 0 of HSV infection (i.e., on the day of infection), 2 days post-infection, or 4 days post-infection. In embodiments, an anti-viral agent (e.g., anti-viral drug acyclovir (ACV)) is administered to the subject from day 4 to 10 post-infection at about 10 mg/kg to about 100 mg/kg.

In embodiments, therapeutic administration includes PSA administered on days 1, 3 and 6 post HSV infection by PO, IP or intravenous injection (IV) along with ACV beginning day 4-10 post-infection (pi). Subjects treated with a zwitterionic polysaccharide (e.g., *B. fragilis* capsular polysaccharide A (PSA)) and ACV by this regimen has $F480^+$ macrophages that are characteristically $CD45^{high}$, CNS resident microglia that are $CD45^{int}$ and glial cells that are $CD45^{neg}$. In embodiments, resting macrophages do not express surface CD107a. In embodiments, fatal HSE is prevented by administering to a subject purified a zwitterionic polysaccharide (e.g., *B. fragilis* capsular polysaccharide A (PSA))

prior to the HSV-1 infection (e.g., subject having a latent HSV-1 infection or at risk of primary infection).

In embodiments, a zwitterionic polysaccharide (e.g., *B. fragilis* capsular polysaccharide A (PSA)) is administered prophylactically without ACV treatment to treat viral infection. In embodiments, about 10 μg to about 100 μg of a zwitterionic polysaccharide (e.g., *B. fragilis* capsular polysaccharide A (PSA)) is administered to a subject by different routes prior to (e.g., subject having a latent infection or at risk of primary infection) and following viral (e.g., HSV) infection. In embodiments, a zwitterionic polysaccharide (e.g., *B. fragilis* capsular polysaccharide A (PSA)) is given prophylactically without ACV treatment. In embodiments, about 10 μg to about 100 μg of PSA is administered to a subject by different routes following viral (e.g., HSV) infection. In embodiments, no ACV is administered to the subject treated with a zwitterionic polysaccharide (e.g., *B. fragilis* capsular polysaccharide A (PSA)). In embodiments, the administration route of a zwitterionic polysaccharide (e.g., *B. fragilis* capsular polysaccharide A (PSA)) may be IP (intra-peritoneal); PO (per-oral); or IV (intra-venous). In embodiments, the administration route is transdermal, subcutaneous, intra-muscular, intra-thecal, intra-ocular, intranasal, transmucosal, sublabial, insufflation, enteral, suppository, intra-arterial, intra-articular, intra-cerebral, intracranial, or intravitreal.

Figure 3A:
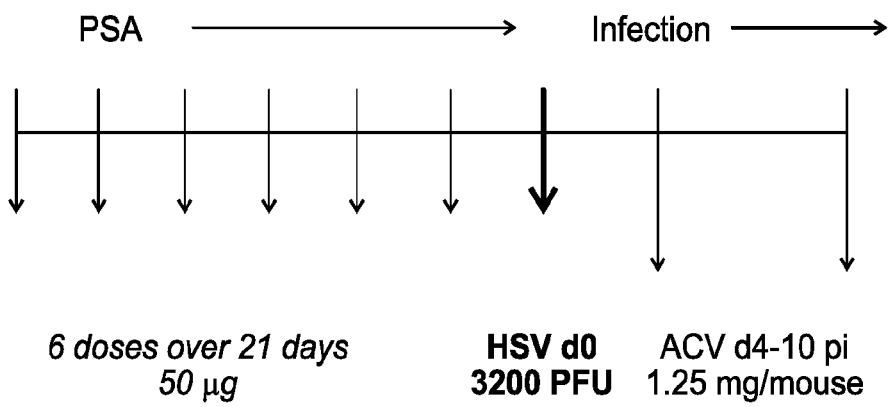
FIGS. 3A-3C depict a schematic, percent survival graph of PSA administration prophylactically with ACV treatment, and CNS inflammation in Rag mice due to absence of T and B cells.

In embodiments, a zwitterionic polysaccharide (e.g., *B. fragilis* capsular polysaccharide A (PSA)) is administered prophylactically with ACV treatment to treat viral infection. In embodiments, doses of a zwitterionic polysaccharide (e.g., *B. fragilis* capsular polysaccharide A (PSA)) are given to subjects prior to HSV infection. In embodiments, six doses of about 10 μg-about 100 μg of a zwitterionic polysaccharide (e.g., *B. fragilis* capsular polysaccharide A (PSA)) are given to a subject over 3 weeks prior to HSV infection on day zero. Six doses of about 10 μg-about 100 μg of a zwitterionic polysaccharide (e.g., *B. fragilis* capsular polysaccharide A (PSA)) are given prior to and during infection as shown in FIG. 3A, or a second regimen involved PSA administration at 8 days before infection, 6 days before infection, 3 days before infection, on the day of infection, 2 days post-infection, 4 days post-infection. The post-infection therapeutic regimen includes PSA administered day 1, day 3, day 6 post-infection, with ACV administered from day 4 post-infection. At day 4 post-HSV infection, 1.25 mg of ACV is administered by IP injections daily for 7 days.

In embodiments, PSA that is administered IP on day 1, day 3, day 6, with ACV administered from day 4 post-infection, to treat viral infection. In other embodiments, a zwitterionic polysaccharide (e.g., *B. fragilis* capsular polysaccharide A (PSA)) interacts with intestinal immune cells and that protection by PSA requires B and/or T cells. In other embodiments, a zwitterionic polysaccharide (e.g., *B. fragilis* capsular polysaccharide A (PSA)) interacts with intestinal immune cells and that protection by a zwitterionic polysaccharide (e.g., *B. fragilis* capsular polysaccharide A (PSA)) requires B cells. In other embodiments, a zwitterionic polysaccharide (e.g., *B. fragilis* capsular polysaccharide A (PSA)) interacts with intestinal immune cells and that protection by a zwitterionic polysaccharide (e.g., *B. fragilis* capsular polysaccharide A (PSA)) requires T cells. In other embodiments, a zwitterionic polysaccharide (e.g., *B. fragilis* capsular polysaccharide A (PSA)) interacts with intestinal immune cells and that protection by a zwitterionic polysaccharide (e.g., *B. fragilis* capsular polysaccharide A (PSA)) requires B and T cells.

Reduction of CNS inflammation by a zwitterionic polysaccharide (e.g., *B. fragilis* capsular polysaccharide A (PSA)) requires T and B cells. In embodiments, CNS inflammation in subjects is treated with a zwitterionic polysaccharide (e.g., *B. fragilis* capsular polysaccharide A (PSA)) in combination with an agent that induces T and B cells.

In embodiments, a subject is treated with a zwitterionic polysaccharide (e.g., *B. fragilis* capsular polysaccharide A (PSA)) resulting in suppression of spontaneous degranulation in monocytes. Monocytes isolated from blood (FIG. 4B) and spleen (FIG. 4C) from a zwitterionic polysaccharide (e.g., *B. fragilis* capsular polysaccharide A (PSA)) treated subject at day 6 post-viral (e.g., HSV) infection show reduced spontaneous degranulation, and limited degranulation following stimulation with HSV antigen. In embodiments, monocytes isolated from blood and spleen from PSA treated subjects post-viral infection show reduced spontaneous degranulation, and limited degranulation following stimulation with HSV antigen.

In embodiments, a zwitterionic polysaccharide (e.g., *B. fragilis* capsular polysaccharide A (PSA)) is administered to a subject to reduce CNS inflammation. In embodiments, administration of a zwitterionic polysaccharide (e.g., *B. fragilis* capsular polysaccharide A (PSA)) reduces CNS inflammation in subjects. In embodiments, administration of a zwitterionic polysaccharide (e.g., *B. fragilis* capsular polysaccharide A (PSA)) to a subject to treat CNS inflammation results in reduced CNS infiltration of $CD45^{high}$ infiltrating leukocytes in the brainstem, reduced $CD11b^+$ cells within brainstem of $CD45^{high}$ infiltrating cells, and reduced inflammatory monocytes (IM) expressing high levels of Ly6C or CD107a/b within brainstem $CD45^{high}$ $CD11b^+$ monocytes. In contrast, the level of CD8 or CD4 T cells within $CD45^{high}$ infiltrating cells is increased in the brainstem after PSA administration.

Figure 8A:
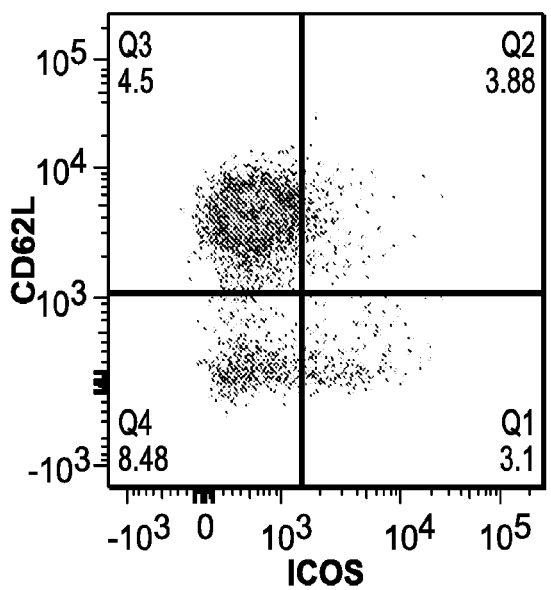
FIGS. 8A-8G depict ICOS+ CD4+ T cells in blood and spleen.
Figure 8B:
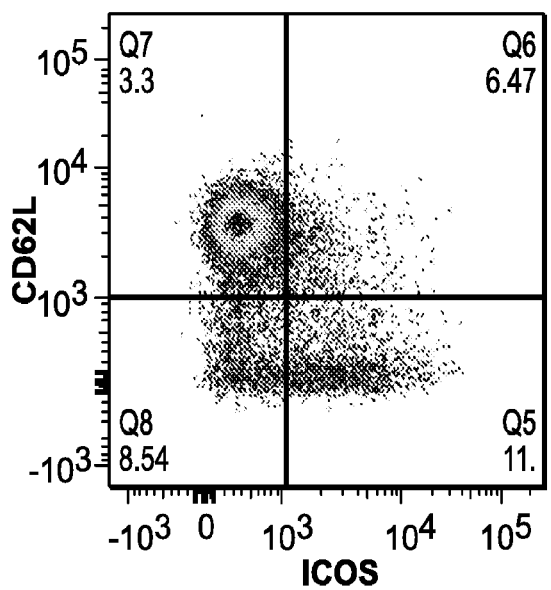
Figure 8C:
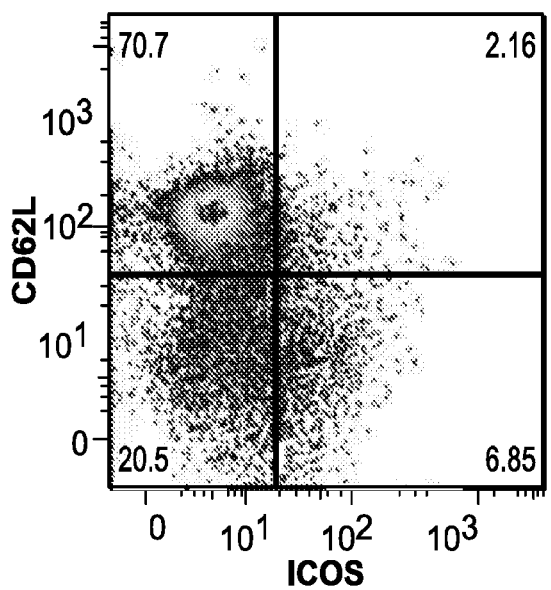
Figure 8D:
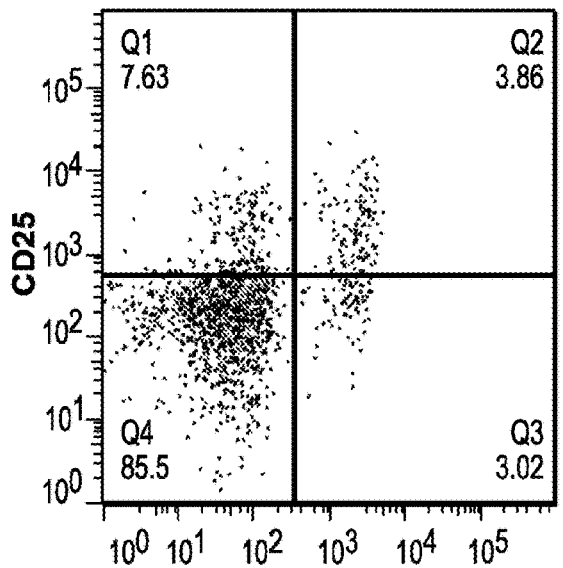
Figure 8E:
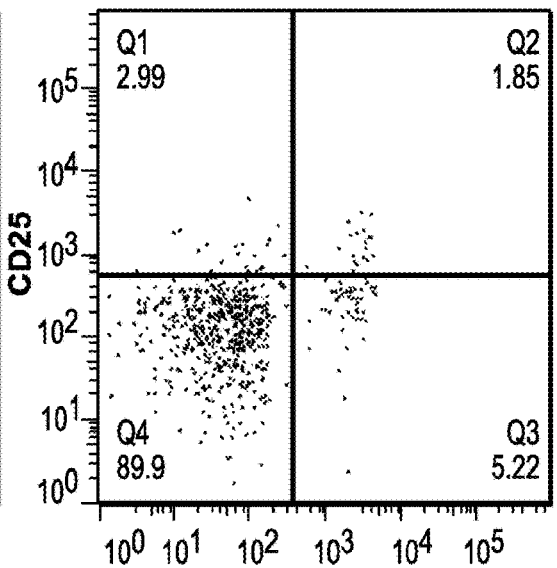
Figure 8F:
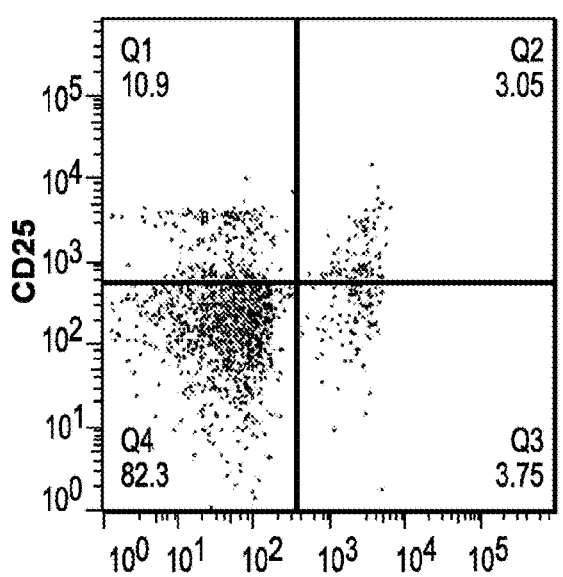
Figure 8G:
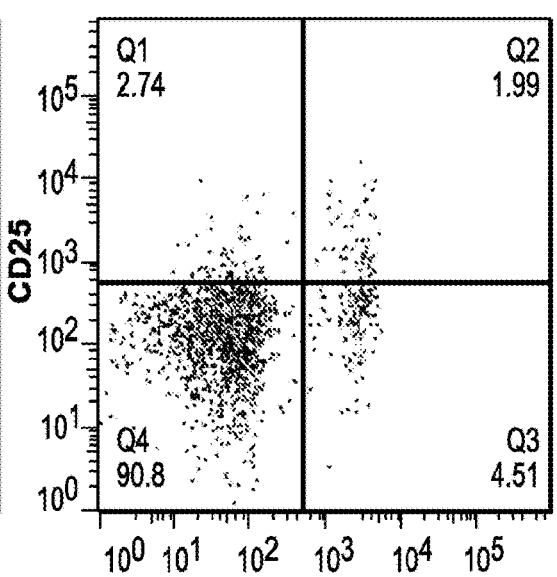

In embodiments, administration of a zwitterionic polysaccharide (e.g., *B. fragilis* capsular polysaccharide A (PSA)) to subjects to treat HSV infection results in ICOS+ CD4+ T cells in the blood and/or spleen. In embodiments, spleen and blood cells are isolated at day 6 post-infection from subjects treated with a zwitterionic polysaccharide (e.g., *B. fragilis* capsular polysaccharide A (PSA)) (by the oral route). FIGS. 8A-8B show FACS plots depicting CD4 T cells in blood and spleen of a zwitterionic polysaccharide (e.g., *B. fragilis* capsular polysaccharide A (PSA)) treated subjects showing an activated phenotype ICOS expression by $CD62^{low}$ cells. FIG. 8C shows a FACS plot from spleen of PBS treated subjects showing $CD62L^{low}$ cells positive for ICOS expression. FIGS. 8D-8G depict graphs of cells from cervical lymph nodes (CLN) (FIGS. 8D and 8F) and spleen (FIGS. 8E and 8G) isolated from subjects treated with PSA and analyzed for CD25 and FoxP3 expression at day 6 post-infection.

Figure 9A:
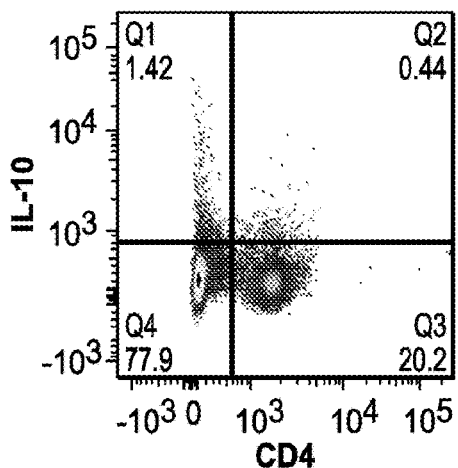
FIGS. 9A-9E depict FACS of cytokine secretion by T cells from spleens of PSA treated mice.
Figure 9B:
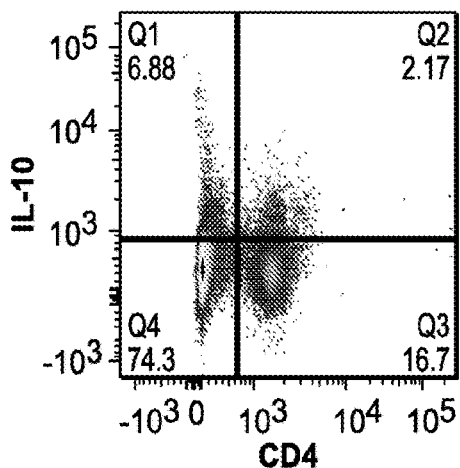
Figure 9C:
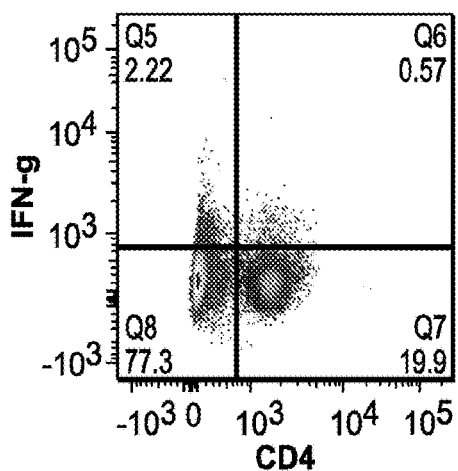
Figure 9D:
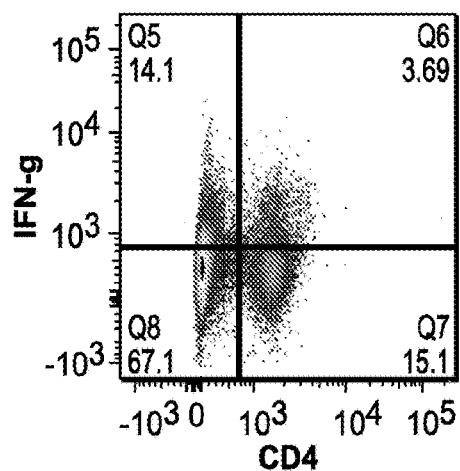
Figure 9E:
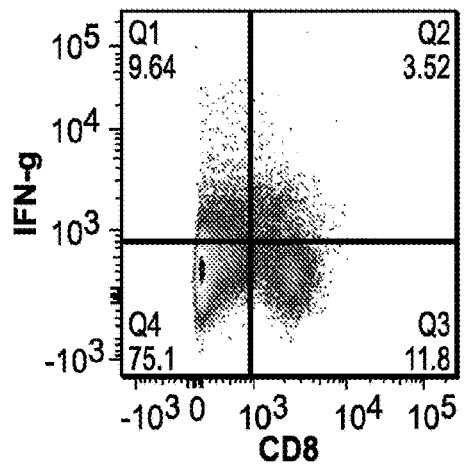

In embodiments, administration of a zwitterionic polysaccharide (e.g., *B. fragilis* capsular polysaccharide A (PSA)) to subjects to treat HSV infection stimulates cytokine secretion by T cells. In embodiments, subjects are given one to six doses of PSA orally and given ACV starting from day 4 post-infection. At day 6 post-infection, spleen cells are isolated and T cells are analyzed for intracellular cytokine secretion by flow cytometry following antigen stimulation. FIGS. 9A and 9B show that CD4 T cells secrete IL-10 in response to stimulation. FIGS. 9C-9E show IFN gamma secretion.

Figure 14A:
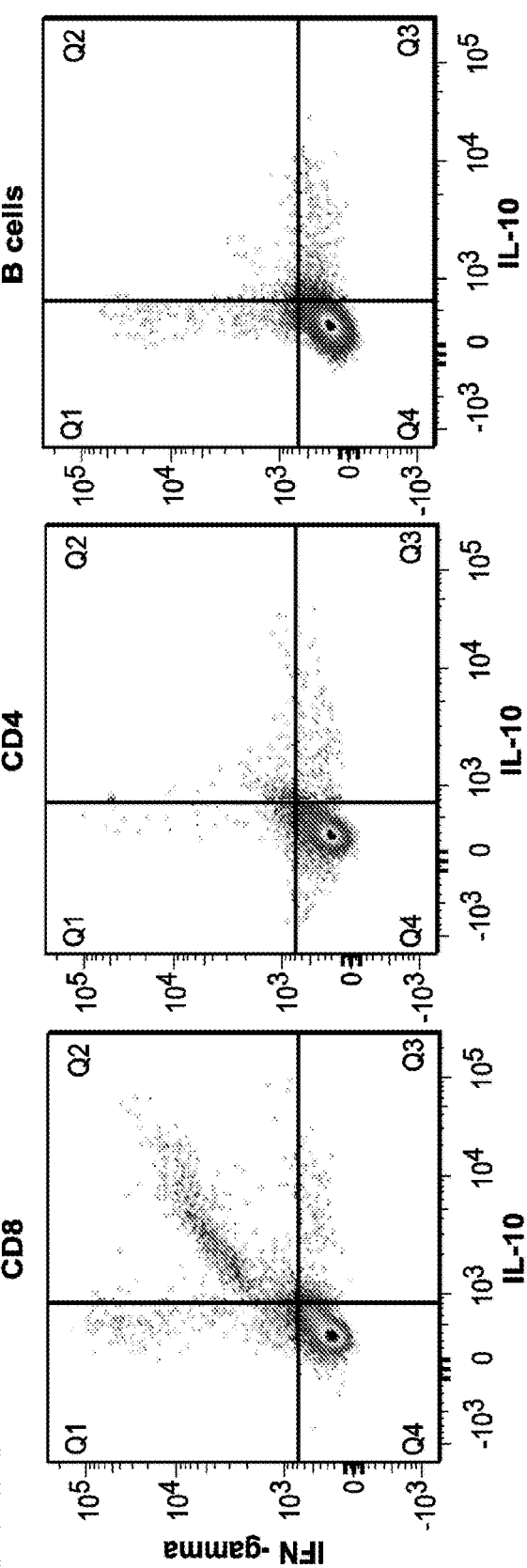
FIGS. 14A-14B depict FACS and bar plots of T and B cells.
Figure 14B:
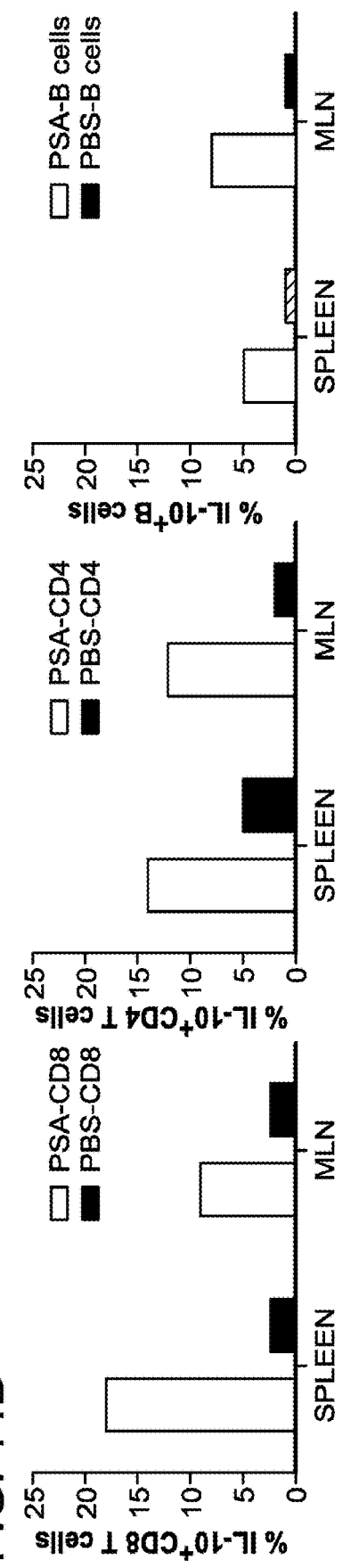

In embodiments, administration of a zwitterionic polysaccharide (e.g., *B. fragilis* capsular polysaccharide A (PSA)) to subjects to treat HSV infection results in increased IL-10 secretion. One to six doses of a zwitterionic polysaccharide (e.g., B. fragilis capsular polysaccharide A (PSA)) are given orally to subjects prior to or after HSV infection at day 0 with/without ACV from day 4 pi. In embodiments, a zwitterionic polysaccharide (e.g., B. fragilis capsular polysaccharide A (PSA)) increases IL-10 secreting T and/or B cells, as depicted in FIGS. 14A-14B. FIG. 14A shows representative FACS plots of IFN-gamma and IL-10 secreting CD8 (left), CD4 (middle) and B cells (right) isolated from spleens of uninfected subjects after 6 doses of oral PSA treatment. FIG. 14B shows bar plots depicting IL-10 secreting CD8 (left) and CD4 T cells (middle) and B cells (right) in the mesenteric lymph nodes (MLN) and spleen of uninfected subjects after 6 doses of oral PSA treatment.

Figure 11:
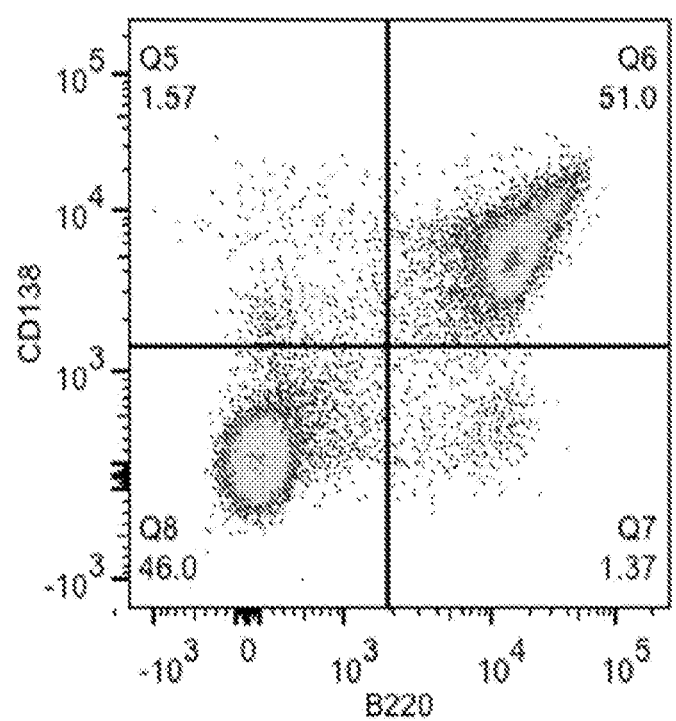
FIG. 11 depicts FACS of spleen cells from PSA treated mice with B220 and CD138 staining.

In embodiments, administration of a zwitterionic polysaccharide (e.g., B. fragilis capsular polysaccharide A (PSA)) to subjects results in splenic B cells with a phenotype representative of immature B cells. In embodiments, splenic B cells isolated from a zwitterionic polysaccharide (e.g., B. fragilis capsular polysaccharide A (PSA)) treated subjects have a plasmablast phenotype. Subjects are given one to six doses of a zwitterionic polysaccharide (e.g., B. fragilis capsular polysaccharide A (PSA)) orally prior to and/or after HSV infection with/without ACV from day 4 pi. At day 6 pi, spleen cells are isolated and analyzed for B cell phenotype. In embodiments, B cells of a zwitterionic polysaccharide (e.g., B. fragilis capsular polysaccharide A (PSA)) treated subjects express a highly activated secretory plasmablast phenotype, CD138 (FIG. 11).

In embodiments, the immunomodulatory effects of a zwitterionic polysaccharide (e.g., B. fragilis capsular polysaccharide A (PSA)) is dependent on B cells and/or T cells. One to six doses of a zwitterionic polysaccharide (e.g., B. fragilis capsular polysaccharide A (PSA)) are administered orally to the B cell depleted subjects infected with HSV. At day 4 post-infection, subjects receive ACV by IP injections. Survival in B cell depleted and non-B cell depleted subjects is compared following HSV infection. In embodiments, B cells and/or T cells are essential for PSA mediated protection in HSV infected subjects.

In embodiments, administration of a zwitterionic polysaccharide (e.g., B. fragilis capsular polysaccharide A (PSA)) to subjects results in accumulation of PSA+ SIGNR1+ dendritic cells (DCs) and/or PMNs in the spleen. PSA+SIGNR1+DCs and PMNs accumulate in the spleen over 24 hours following oral administration. In embodiments, plasmacytoid dendritic cells (DCs) and plasmablasts bind PSA and induce IL-10 secretion by CD45+ IEL T cells in subjects.

In embodiments, administration of a zwitterionic polysaccharide (e.g., B. fragilis capsular polysaccharide A (PSA)) to subjects results in Tregs activation. In embodiments, Tregs express FoxP3 in a zwitterionic polysaccharide (e.g., B. fragilis capsular polysaccharide A (PSA)) treated subjects. In embodiments, a zwitterionic polysaccharide (e.g., B. fragilis capsular polysaccharide A (PSA)) increases accumulation of regulatory T cells in lymph nodes of subjects. In embodiments, a zwitterionic polysaccharide (e.g., B. fragilis capsular polysaccharide A (PSA)) increases accumulation of regulatory T cells in mesenteric lymph nodes of subjects.

In embodiments, inflammation is decreased in a subject by administering a composition including an effective amount of a zwitterionic polysaccharide (e.g., B. fragilis capsular polysaccharide A (PSA)) (including active fragments thereof). In embodiments, inflammation is decreased in a subject by administering a composition including an effective amount of a zwitterionic polysaccharide (e.g., B. fragilis capsular polysaccharide A (PSA)) (including active fragments thereof) and an effective amount of an anti-viral agent.

In embodiments, a zwitterionic polysaccharide (e.g., B. fragilis capsular polysaccharide A (PSA)) (including active fragments thereof) is used to treat viral infection. In embodiments, a zwitterionic polysaccharide (e.g., B. fragilis capsular polysaccharide A (PSA)) (including active fragments thereof) is used to treat neuroinflammation. In embodiments, a zwitterionic polysaccharide (e.g., B. fragilis capsular polysaccharide A (PSA)) (including active fragments thereof) is used to modulate the immune response in a subject having a dormant (latent) viral infection. In embodiments, a zwitterionic polysaccharide (e.g., B. fragilis capsular polysaccharide A (PSA)) (including active fragments thereof) is used to treat encephalitis, e.g., HSV encephalitis (HSE) in a subject. In embodiments, a zwitterionic polysaccharide (e.g., B. fragilis capsular polysaccharide A (PSA)) (including active fragments thereof) is used to treat Herpes stromal keratitis (HSK) in a subject. In embodiments, the subject is undergoing treatment with a zwitterionic polysaccharide (e.g., B. fragilis capsular polysaccharide A (PSA)) to treat a symptomatic viral infection. In embodiments, the subject is undergoing treatment with PSA to treat reactivation of a latent viral infection.

The following examples are provided as illustrations of various embodiments of the disclosure but are not meant to limit the disclosure in any manner.

EXAMPLES

Example 1: Acyclovir (ACV) Cannot Prevent Lethal HSV Encephalitis (HSE) when Given at Day 4 Post Infection (pi)

Mouse and Virus Inoculation

129S6 Wild Type (WT), 129 FoxP3-GFP and IL-10 knock-out (KO) mice were bred. Male and female mice aged 6-10 weeks were infected with HSV-1 strain 17+ (HSV). Mice were sedated with ketamine (120 mg/kg) and xylazine (10 mg/kg) prior to HSV inoculation by corneal scarification with 3200 PFU, equivalent to 10 LD50 for the 129 WT strain.

Administration of PSA

Prophylactic administration: six doses of 50 µg of PSA in sterile PBS was given as indicated-orally (PO), or intraperitoneally (IP) over 3 weeks prior to HSV infection. Additionally, six doses of PSA were given IP on 9 days before HSV infection, 6 days before HSV infection, 3 days before HSV infection, day 0 of HSV infection (i.e., on the day of infection), 2 days post-infection, and 4 days post-infection. Mice received either PBS or the anti-viral drug acyclovir (ACV) from day 4 to 10 post-infection at 50 mg/kg. Therapeutic administration: PSA was administered on days 1, 3 and 6 post HSV infection by PO, IP or intravenous injection (IV) along with ACV beginning day 4-10 post-infection (pi).

Flow Cytometric Analysis

Single cell suspensions isolated from either brain, BS, spleen or cervical lymph nodes were blocked with a 10% mixture of normal mouse, rat and horse serum and rat anti-mouse CD16/32 for 15 min. prior to incubation with antibodies (Abs) to determine cell surface expression of various markers. F480+ macrophages were characteristically $CD45^{high}$, CNS resident microglia $CD45^{int}$ and glial cells CD45$^{neg}$. Activation of macrophages and microglia was determined by their mean fluorescence intensity (MFI) of expression of MHC class II molecules. Efficiency of degranulation by macrophages was determined in vitro in the absence of Ag stimulation or following stimulation of cells for 5 hr with heat-killed HSV in the presence of anti-CD107a/b antibodies to capture cell surface associated LAMPs. Resting macrophages did not express surface CD107a. Neutrophils were determined by their SSC$^{high}$, Ly6-G$^+$, MHC II$^-$, F480$^-$ phenotype. CD4$^+$ Tregs were determined by reactivity to CD25 and FoxP3 GFP expression in the 129 FoxP3 GFP reporter mice. MHC I tetramers (H-2$^b$) were used to measure the immunodominant HSV gB peptide (gB$_{498-505}$: SSIEFARL) specific CD8 T cells following HSV infection. ICOS expressing CD62L$^{low}$ CD4+ T cells secrete the majority of IL-10 and IFN-gamma following HSV infection. Intracellular cytokine detection was performed using Cytofix/Cytoperm™ Plus kit containing golgistop (BD Biosciences) according to manufacturer's instructions. Briefly, following stimulation with PMA+Ionomycin (for CD4s) or HSV gB SSIEFARL peptide (for CD8s) in the presence of Golgistop containing Brefeldin A, cells were stained for surface expression of CD4 and CD8 before permeabilization using cytofix/cytoperm buffers. Intracellular cytokine expression was then detected using fluorescent conjugated IL-10 or IFN-gamma antibodies. Cells were acquired on a BD Fortessa flow cytometer and flow cytometry analysis was performed using Flowjo software (Treestar Inc.).

Control mice pretreated with balanced saline solution (PBS) developed fatal HSE, whereas mice pretreated with purified PSA prior to the HSV-1 infection prevented the development of fatal HSE (FIG. 1).

Example 2: PSA Given Prophylactically without ACV Treatment

Figure 2:
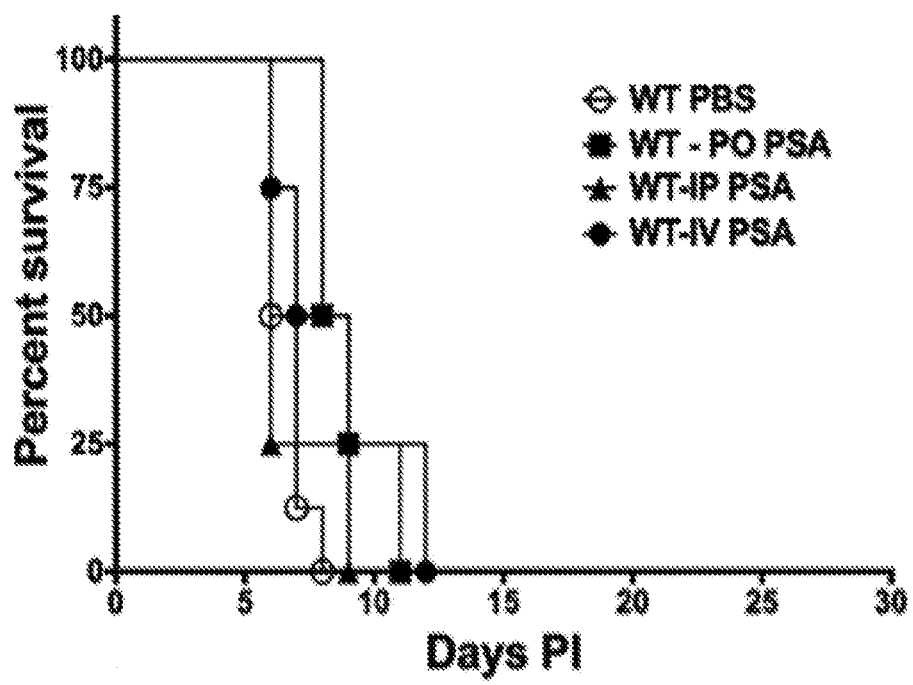
FIG. 2 depicts a percent survival graph of mice prophylactically administered with PSA, but without ACV administration. IP: intraperitoneal; PO: per-oral; IV: intravenous.

50 µg of PSA was administered to 129 WT mice by different routes prior to and following HSV infection. No ACV was given to the mice. The administration routes consisted of IP (intra-peritoneal); PO (per-oral); or IV (intravenous) (FIG. 2).

Example 3: PSA Given Prophylactically with ACV Treatment

Figure 3B:
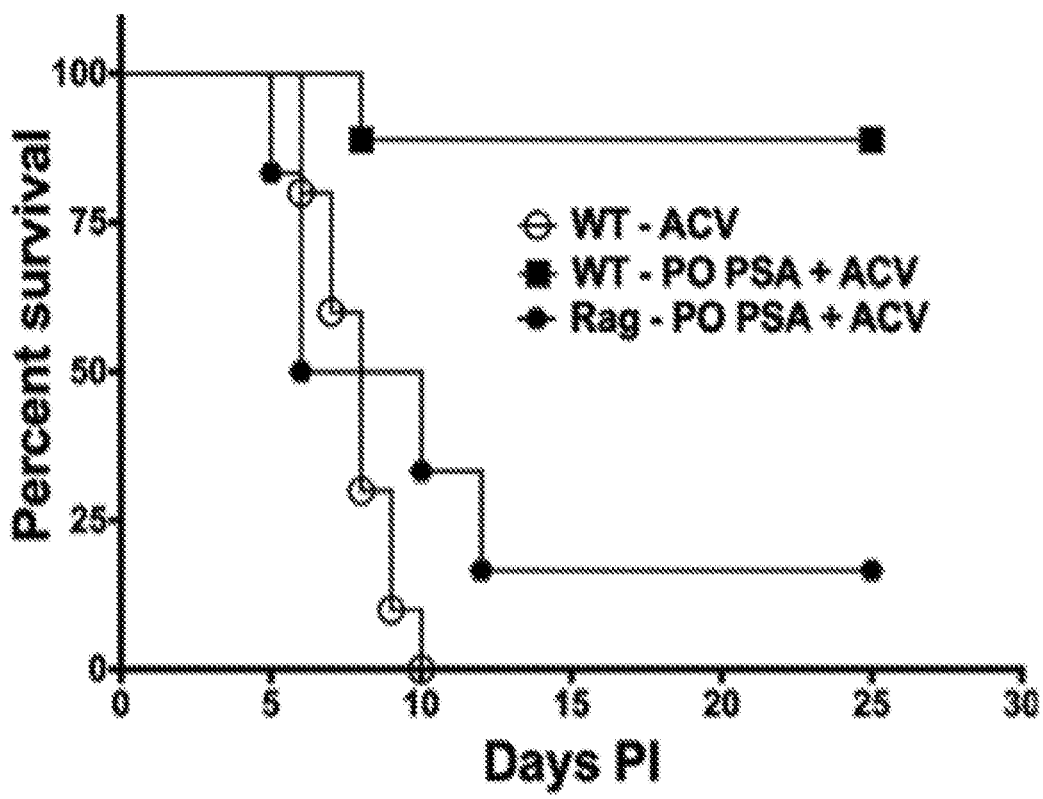

FIG. 3A shows schematic of six doses of 50 µg of PSA given to 129 WT or Rag mice over 3 weeks prior to HSV infection on day zero. Six doses of 50 µg of PSA were given prior to and during infection as shown in FIG. 3A, or a second regimen involved PSA administration at 8 days before infection, 6 days before infection, 3 days before infection, on the day of infection, 2 days post-infection, 4 days post-infection. The post-infection therapeutic regimen included PSA administered day 1, day 3, day 6 post-infection, with ACV administered from day 4 post-infection. At day 4 post-HSV infection, 1.25 mg of ACV was given per mouse by IP injections daily for 7 days. The results showed that this dosage strategy did not protect against HSV infection. PSA administered IP therapeutically day 1, day 3, day 6 with ACV from day 4 post-infection also did not protect against HSV infection, suggesting that PSA might need to interact with intestinal immune cells and that protection by PSA might require B and/or T cells. 129 WT or Rag mice were given PSA as indicated in FIG. 3A prior to the infection. ACV was given starting at day 4 post-infection (FIG. 3B).

Figure 3C:
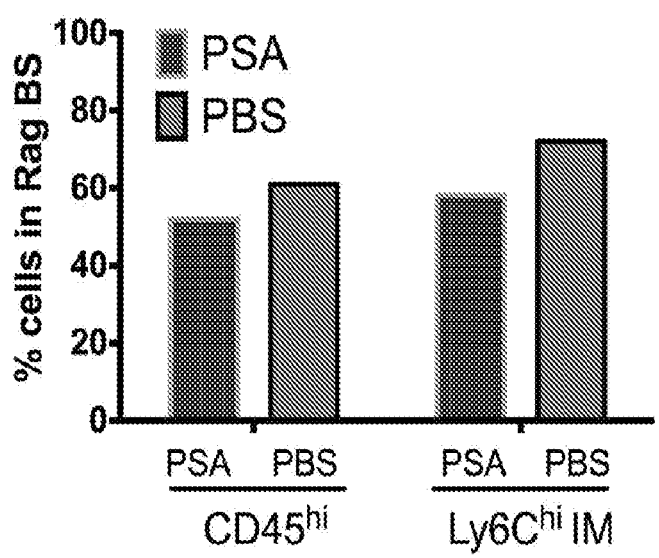

FIG. 3C shows bar plots demonstrating that PSA does not reduce CNS inflammation in Rag mice due to absence of T and B cells. PSA or PBS treated 129 Rag mice (see FIG. 3A) were infected with HSV 17+ strain (3200 PFU), given ACV from day 4 pi for a week and brainstems (BS) were isolated at day 6 pi for analysis of infiltrating leukocytes. Bar plots show increased % CD45$^{high}$ infiltrates and Ly6C$^{high}$ CD11b+ inflammatory monocytes (IM)/CD45$^{high}$ infiltrates in brainstem (BS) of PSA and PBS treated Rag mice.

Example 4: PSA Suppresses Spontaneous Degranulation in Monocytes

Monocytes isolated from blood (FIG. 4B) and spleen (FIG. 4C) from PSA treated mice at day 6 post-infection showed reduced spontaneous degranulation, and limited degranulation following stimulation with HSV antigen.

Example 5: PSA Reduces CNS Inflammation in WT Mice

Figure 5A:
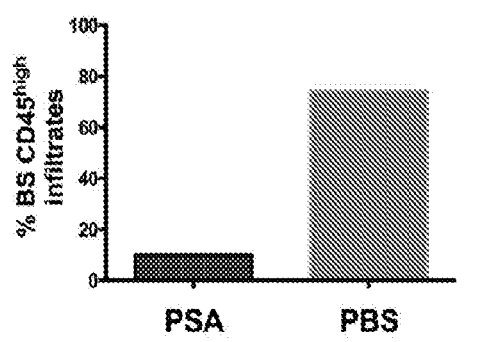
FIGS. 5A-5D depict histograms showing percent of inflammatory monocytes and T cells infiltrating brainstem (BS). The data shows that PSA reduces CNS inflammation in WT mice.
Figure 5B:
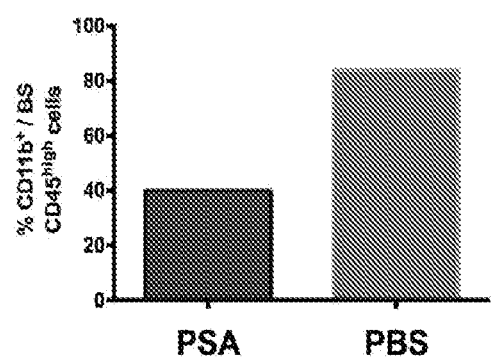
Figure 5C:
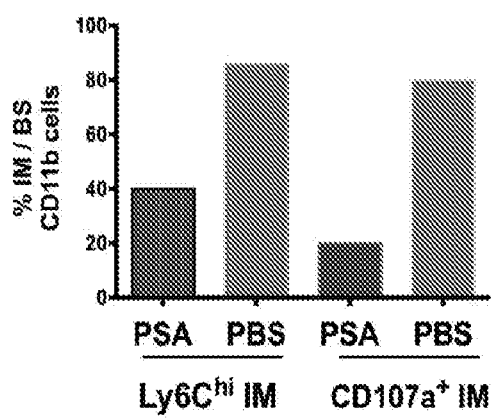
Figure 5D:
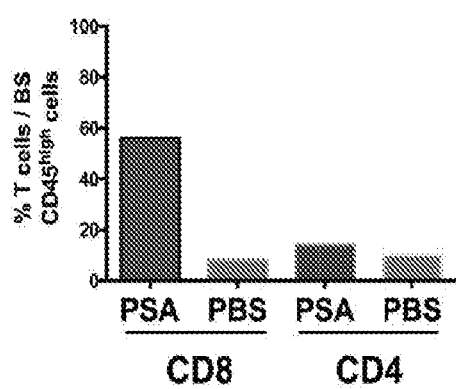

PSA or PBS treated 129 WT mice (see FIG. 3A) were infected with HSV 17+ strain (3200 PFU), given ACV from day 4 pi for a week and brainstems (BS) were isolated at day 6 pi for analysis of infiltrating leukocytes. FIGS. 5A-5D shows bar plots depicting PSA reducing CNS inflammation in wild type mice. FIG. 5A shows differences in % CD45$^{high}$ infiltrating leukocytes in the BS of PSA or PBS treated WT mice. FIG. 5B shows % CD11b$^+$ cells within BS of CD45$^{high}$ infiltrating cells. FIG. 5C shows the % Inflammatory monocytes (IM) expressing high levels of Ly6C or CD107a/b within BS CD45$^{high}$ CD11b$^+$ monocytes. FIG. 5D shows % CD8 or CD4 T cells within CD45$^{high}$ infiltrating cells in the BS of PSA or PBS treated WT mice.

The majority of CD8+ in BS were CD103+. Greater than 70% CD8+ were virus specific based on tetramer staining. Most BS CD8+ CD103+ T cells were CD62L$^{low}$. PSA induced CD4+ ICOS+ T cells in the spleen (56%), and the majority were activated (CD62L$^{low}$, and few are in BS). Approximately 10% of CD4+ ICOS+ T cells produced IL-10 with PMA+ ionomycin stimulation. IL-10 was also produced by other cell types. No change in frequency of Tregs in the spleen or BS was observed.

Example 6: Reduced Inflammatory Monocytes in BS-Day 6 Post-Infection

Figure 6A:
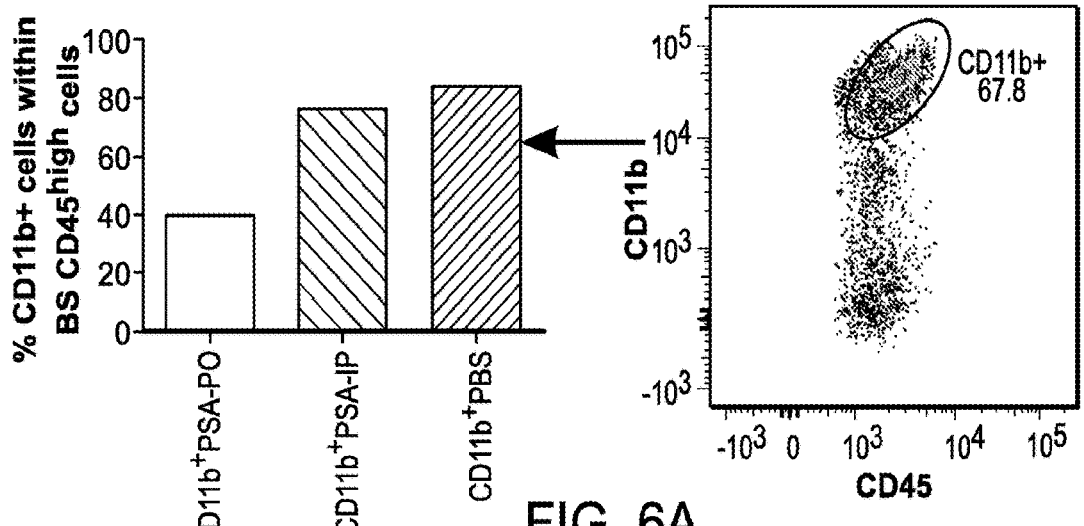
FIGS. 6A-6C depict histograms and florescence activated cell sorting (FACS) plots showing reduced inflammatory monocytes in BS-day 6 post-infection.
Figure 6B:
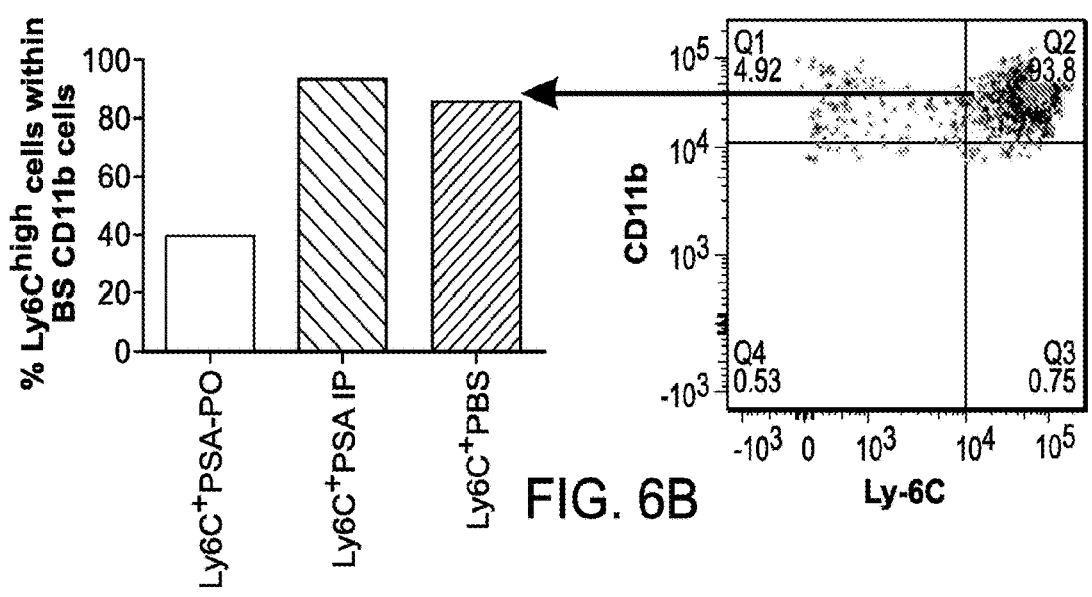
Figure 6C:
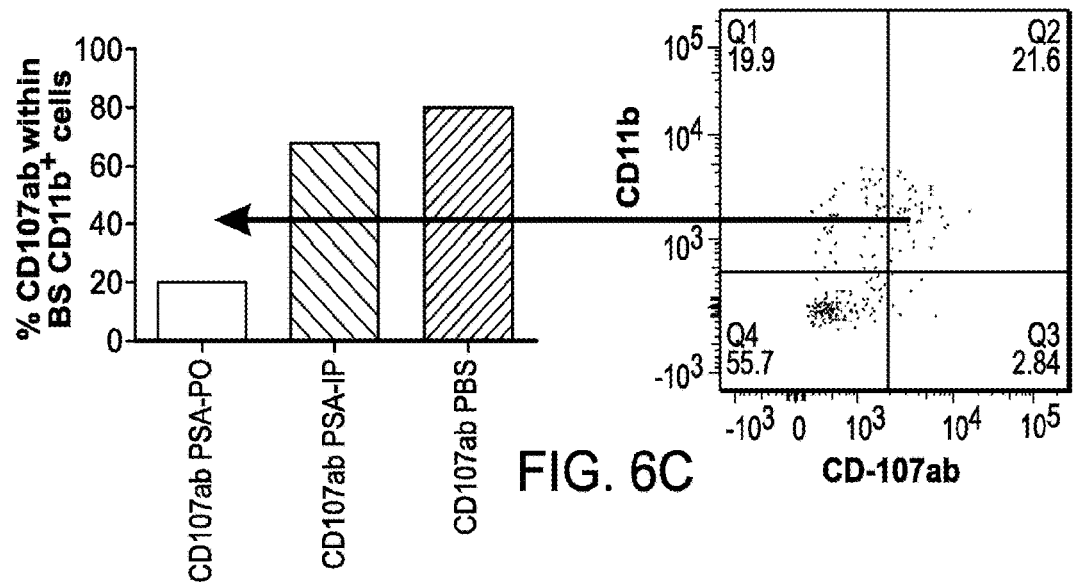
Figure 7A:
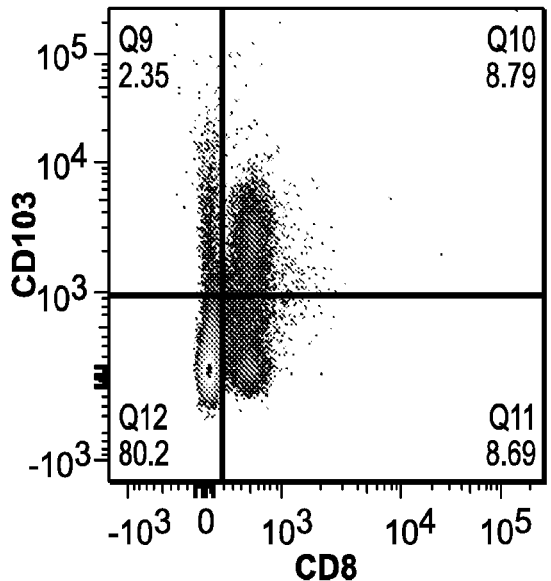
FIGS. 7A-7H depict FACS of CD8+ T cell priming in spleen. At day 6 post-infection, spleen (FIGS. 7A-7D) cells and blood (FIGS. 7E-7H) were analyzed by flow cytometry.
Figure 7B:
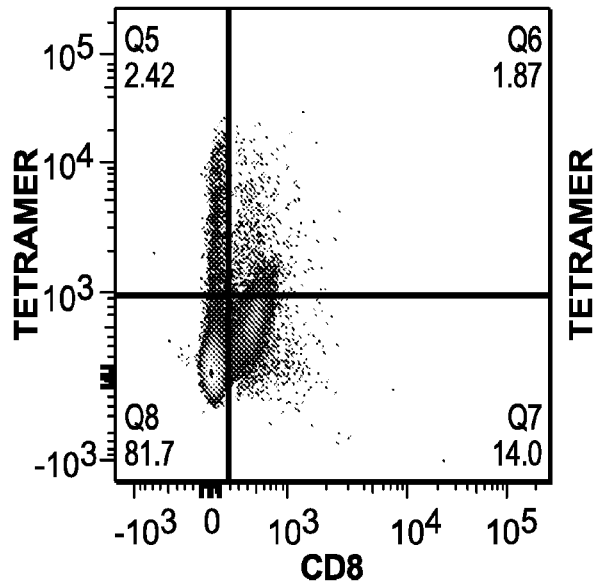
Figure 7C:
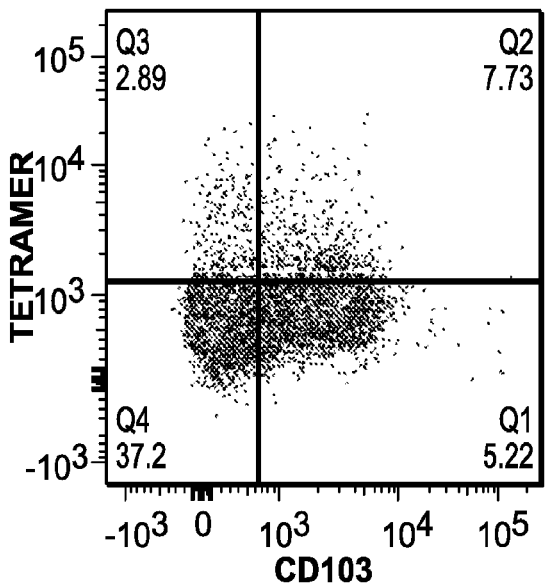
Figure 7D:
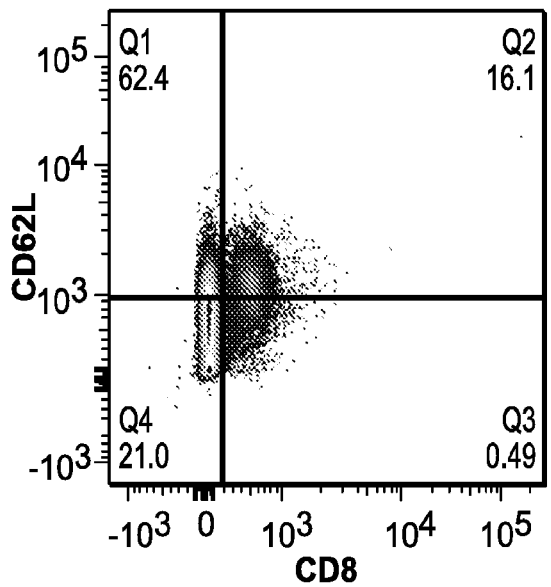
Figure 7E:
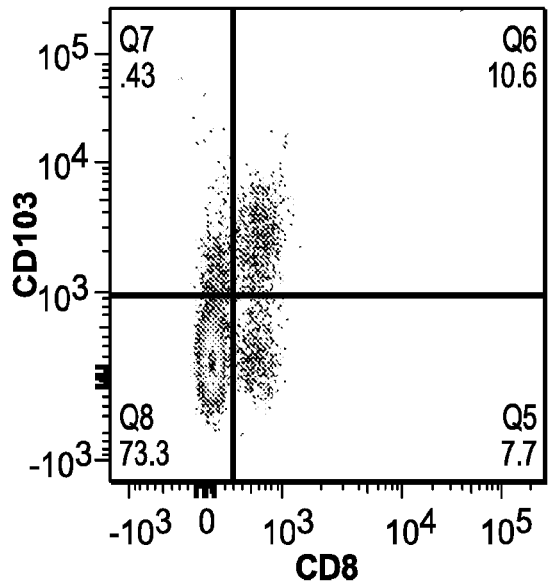
Figure 7F:
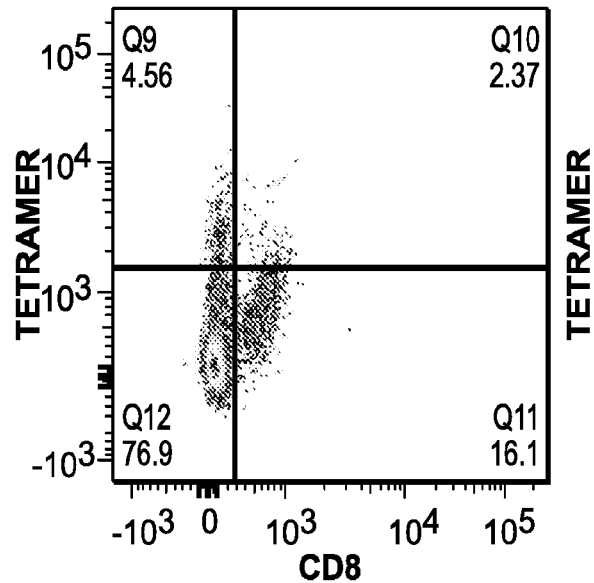
Figure 7G:
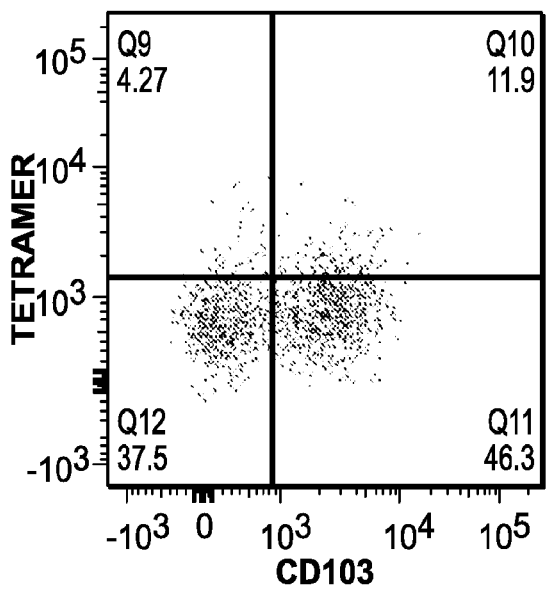
Figure 7H:
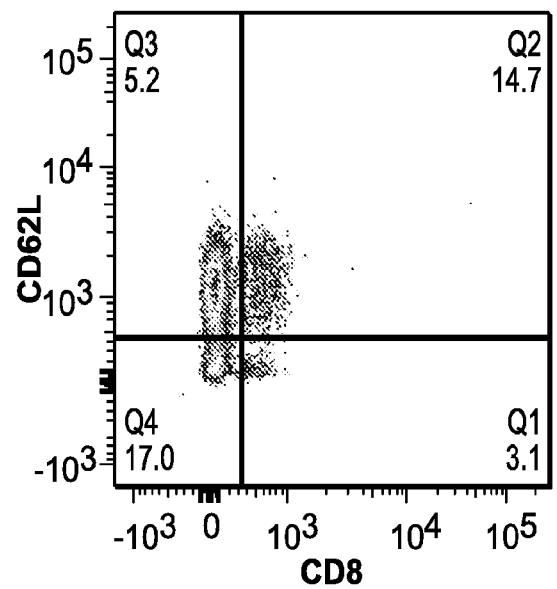

BS mononuclear cells were isolated at day 6 from PSA or PBS treated 129 WT mice were analyzed for percent monocytes with CD45$^{high}$ cells by flow cytometry (FIGS. 6A-C).

Example 7: CD8+ T Cell Priming in Spleen

129 WT mice were given six doses of PSA by the oral route and then infected with HSV and ACV from day 4 post-infection. At day 6 post-infection, spleen (FIGS. 7A-7D) cell and blood (FIGS. 7E-7H) were analyzed by flow cytometry for virus specific CD8 T cells. FIGS. 7A-7D show about 12% of spleen CD9s isolated from spleens of PSA treated 129 WT mice are virus specific, based on H-2$^b$ HSV gB498 tetramer staining and >70% were CD103+. The majority of the activated (i.e. tetramer+) CD103+ CD8+ T cells were CD62L$^{high}$. FIGS. 7E-7H depicts a similar profile to the spleen (FIGS. 7A-7D) CD8 T cells, but shown for blood CD8+ T cells.

Example 8: ICOS+ CD4+ T Cells in the Blood and Spleen

Spleen and blood cells were isolated at day 6 post-infection from 129 WT mice treated with PSA (by the oral route), and HSV infected. FIGS. 8A-8B show FACS plots depicting CD4 T cells in blood and spleen of PSA treated mice showing an activated phenotype ICOS expression by $CD62^{low}$ cells. 56% of $CD62L^{low}$ cells were ICOS+. FIG. 8C shows a FACS plot from spleen of PBS treated mice, showing that only 25% of $CD62L^{low}$ cells are ICOS+. FIGS. 8D-8G depict graphs of cells from cervical lymph nodes (CLN) (FIGS. 8D and 8F) and spleen (FIGS. 8E and 8G) isolated from 129 WT mice treated with either PSA or PBS by the oral route, and analyzed for CD25 and FoxP3 expression at day 6 post-infection.

Example 9: Cytokine Secretion by T Cells from Spleens of PSA Treated Mice

129 WT mice were given six doses of PSA by the oral route and were infected with HSV and given ACV from day 4 post-infection. At day 6 post-infection, spleen cells were isolated and T cells were analyzed for intracellular cytokine secretion by flow cytometry following antigen stimulation (PMA+ionomycin). FIGS. 9A and 9B show that about 11% of CD4s secrete IL-10 in response to stimulation but the majority of IL-10 is produced by other cell types. FIGS. 9C-9E show IFN gamma secretion.

Example 10: Role of IL-10 in Survival

Figure 10:
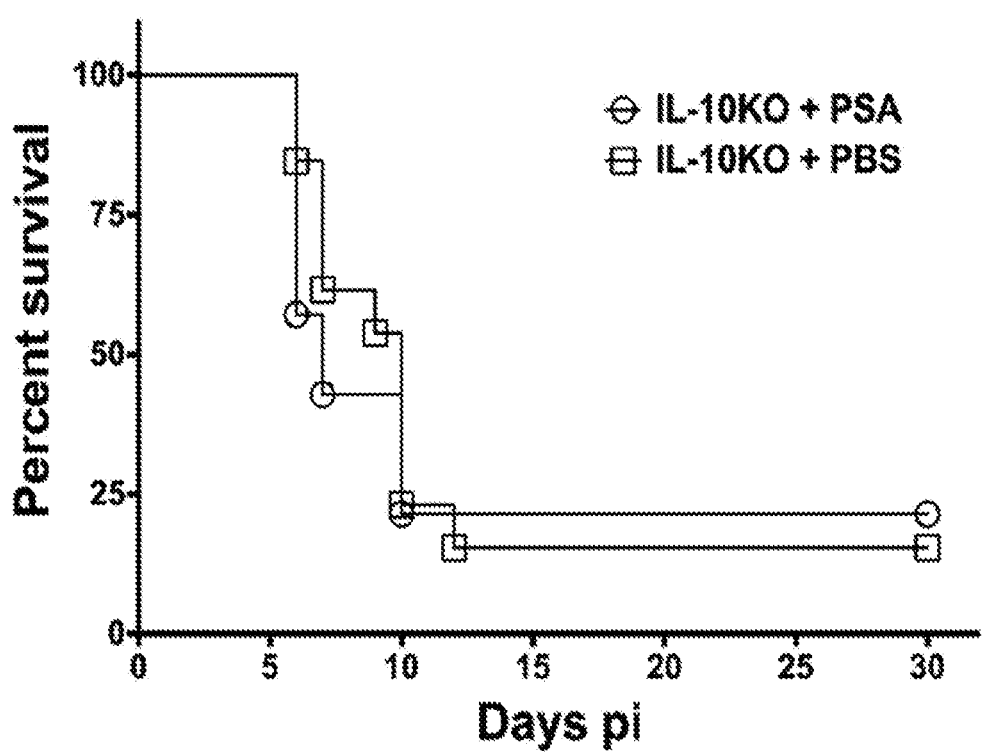
FIG. 10 depicts survival graphs of PSA and PBS (control) treated IL-10 knock-out (KO) mice.

IL-10 knockout mice were treated similar to WT mice. Six doses of PSA or PBS were given orally prior to HSV infection at day 0 and ACV from day 4 pi. Mice were observed for survival (FIG. 10).

PSA increases IL-10 secreting T and B cells, as depicted in FIGS. 14A-14B. FIG. 14A shows representative FACS plots of IFN-gamma and IL-10 secreting CD8 (left), CD4 (middle) and B cells (right) isolated from spleens of uninfected WT mice after 6 doses of oral PSA treatment. FIG. 14B shows bar plots depicting IL-10 secreting CD8 (left) and CD4 T cells (middle) and B cells (right) in the MLN and spleen of uninfected WT mice after 6 doses of oral PSA or PBS treatment.

Example 11: Splenic B Cells Isolated from PSA Treated Mice Have a Plasmablast Phenotype 129 WT mice were given six doses of PSA orally prior to HSV infection and ACV from day 4 pi. At day 6 pi, spleen cells were isolated and analyzed for B cell phenotype; the majority of B cells express a highly activated secretory plasmablast phenotype, CD138 (FIG. 11).

Example 12: Role of B Cells in PSA Dependent Protection

Figure 12:
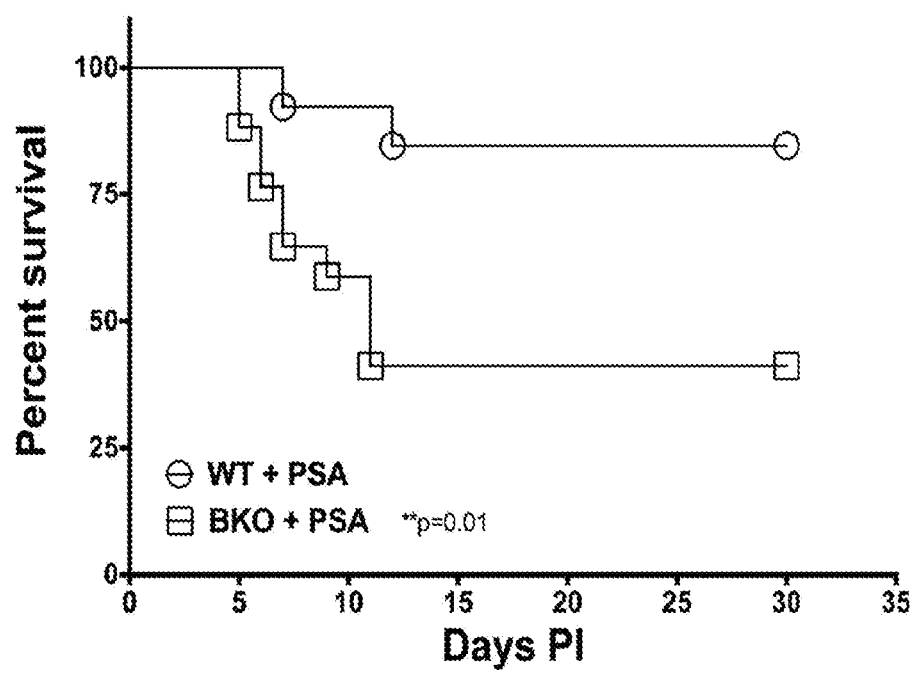
FIG. 12 depicts survival graphs of PSA treated HSV infected WT and B cell knockout (BKO) mice.

B cells were depleted from 129 WT mice by IP injections of anti-mouse CD20 mAb one week prior to the first PSA dose and every 7 days after (FIG. 12). B cell depletion was confirmed in the spleen and blood every 7 days in euthanized mice. Six doses of PSA were administered orally to the B cell depleted mice following which they were infected with HSV 17+ strain by the corneal scarification method. At day 4 post-infection, mice received ACV by IP injections. Survival in B cell knockout and WT mice was compared following HSV infection.

Figure 18:
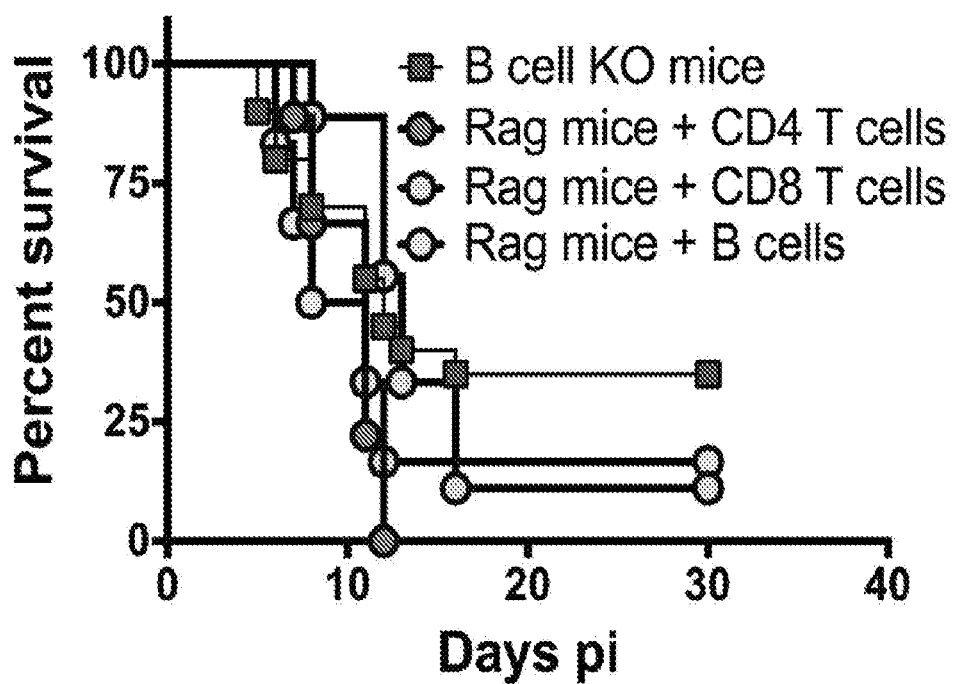
FIG. 18 depicts survival plots of PSA treated knockout mice. Survival of PSA treated B cell knockout (KO) mice or 129 Rag recipients of CD4 T cells, CD8 T cells or B cells are plotted. All mice were infected with HSV 17+ strain and given ACV from day 4 pi.

Survival plots of PSA treated knockout mice are depicted in FIG. 18. Survival of PSA treated B cell knockout (KO) mice or 129 Rag recipients of CD4 T cells, CD8 T cells or B cells are plotted. All mice were infected with HSV 17+ strain and given ACV from day 4 pi. These results demonstrate that B cells and T cells are essential for PSA mediated protection.

Figure 13D:
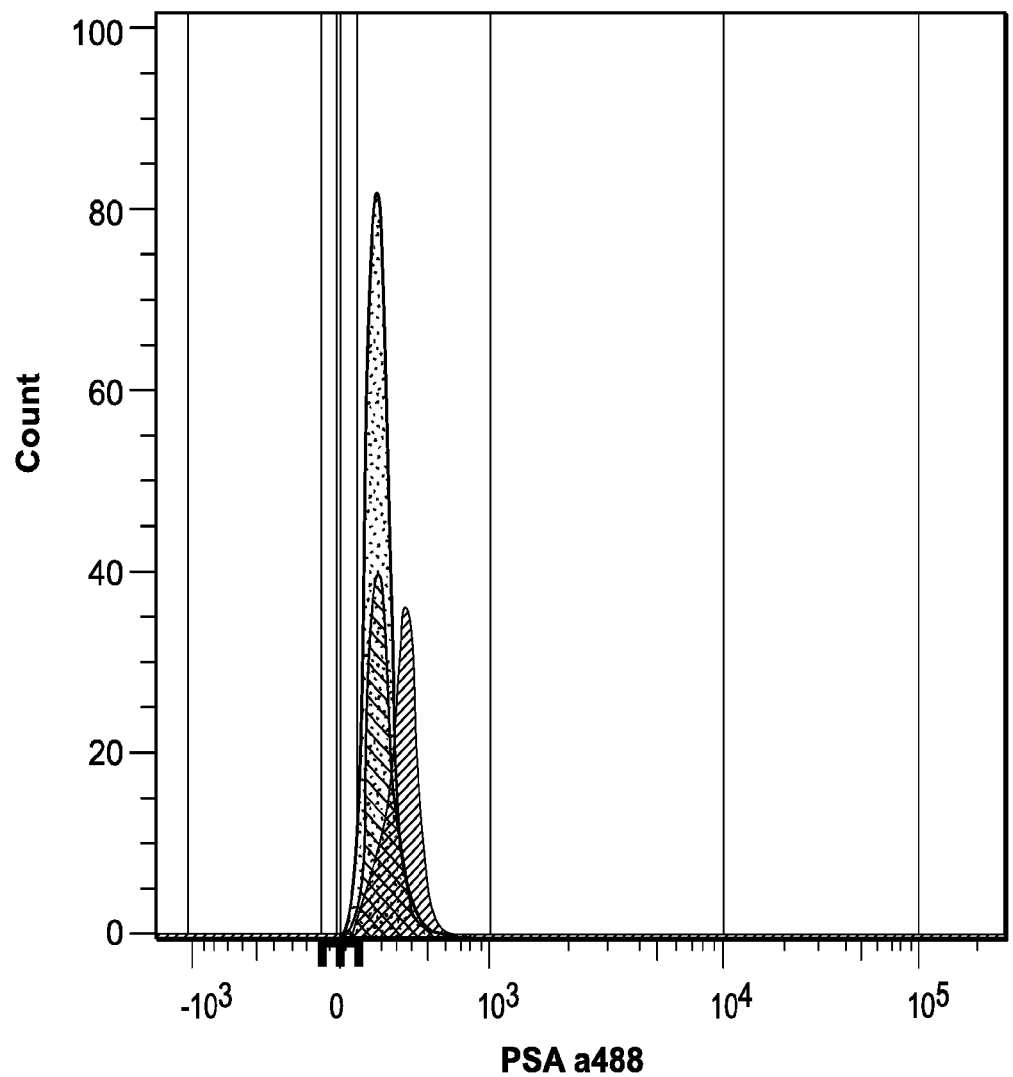

Example 13: PSA+SIGNR1+DCs and PMNs Accumulate in the Spleen Over 24 Hours Following Oral Gavage PSA conjugated to Alexa 488 fluorescent dye was given by oral gavage to 129 WT mice (FIGS. 13A-D). At 2, 4 and 24 hours post gavage, mesenteric lymph nodes (MLN), intestine and spleen were removed and cells were analyzed for PSA binding by flow cytometry or immune-fluorescence. FIGS. 13A-13C depicts data for flow cytometric binding of PSA to DCs. FIGS. 13A-13C shows time lapse and increased accumulation of PSA+DCs in the spleen. FIG. 13D depicts neutrophils showing slight binding or phagocytosis of PSA binding cells at 24 hours in one MLN. No other cells were positive for PSA in that MLN.

Figures 17A, 17B:
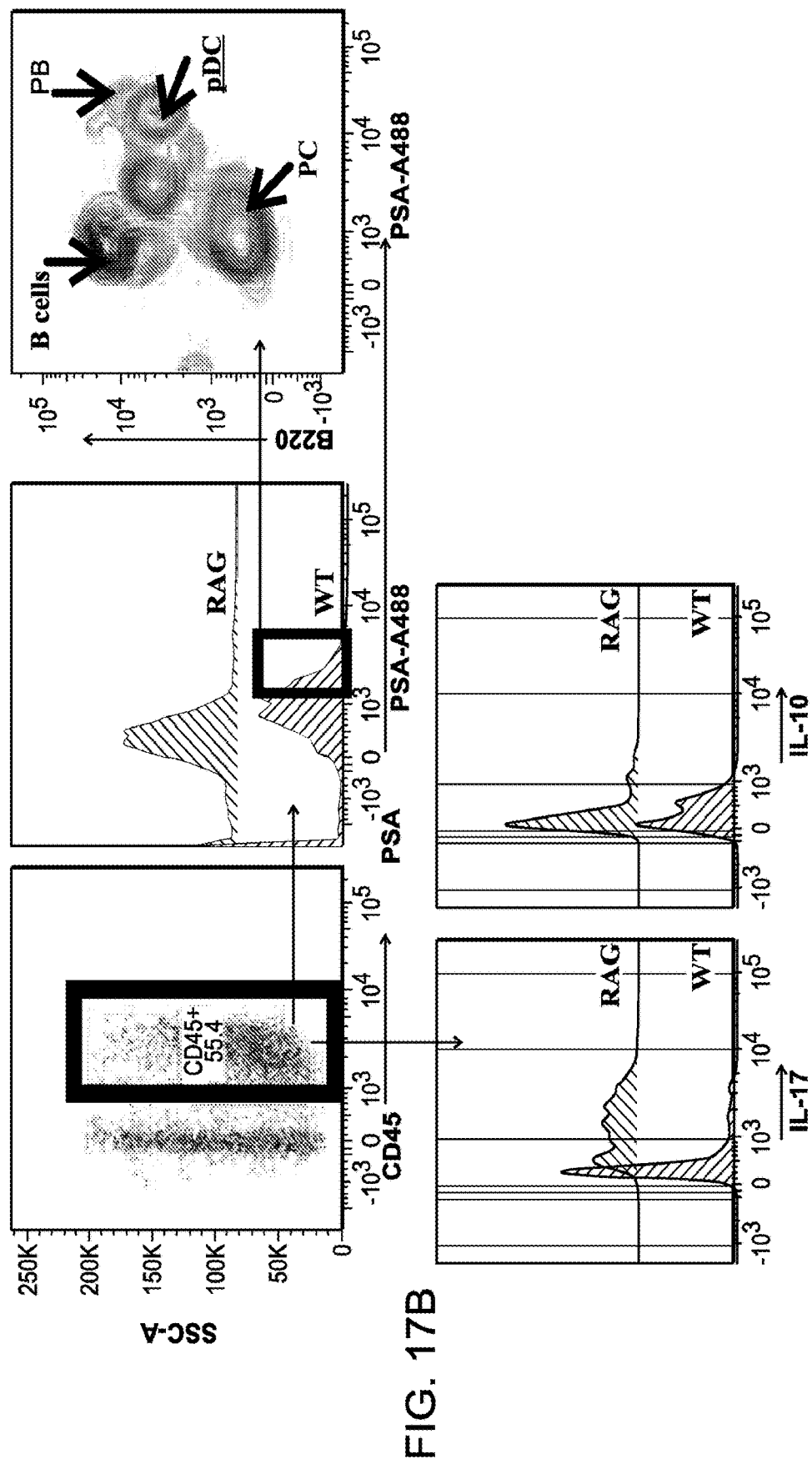
FIGS. 17A-17B depict FACS plots showing that plasmacytoid dendritic cells (pDCs) and plasmablasts (PB) bind PSA and induce IL-10 secretion by CD45+ IEL T cells in WT but not Rag mice.

Binding of oral fluorescent tagged PSA to $CD45^+$ (boxed) intra-epithelial lymphocytes (left) isolated from ileum of treated 129 WT mice and Rag mice (middle); Middle plot gated on boxed $CD45^+$ IEL cells in left plot are depicted in FIG. 17A. WT $CD45^+$ cells binding PSA (Gated on PSA binding WT $CD45^+$ IEL shown in box in middle plot) were mainly $CD138^+$ $B220^+$ plasmablasts (PB) and $PDCA1^+$ $B220^+$ $CD11c^+$ plasmacytoid DCs (pDC); $CD138^+$ $B220^{low}$ plasma cells (PC), B cells and other immune cells showed minimal binding (right plot). FIG. 17B shows IL-17 (left plot) and IL-10 secretion (right plot) from PSA stimulated $CD45^+$ IEL (shown in box in left plot in FIG. A) isolated from ileum of 129 WT or Rag mice. These results demonstrate that plasmacytoid dendritic cells (DCs) and plasmablasts bind PSA and induce IL-10 secretion by CD45+ IEL T cells in wild type but not Rag mice.

Example 14: Role of Tregs in PSA Treated Mice

Figure 15A:
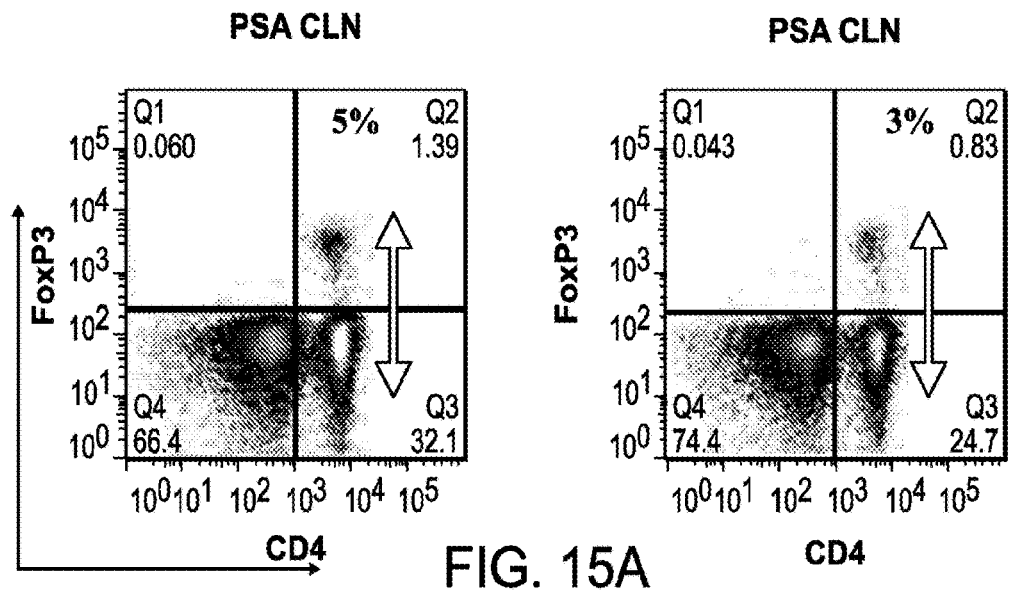
FIGS. 15A-15C depict FACS plots of FoxP3 Tregs having a functional phenotype in PSA treated mice.
Figure 15B:
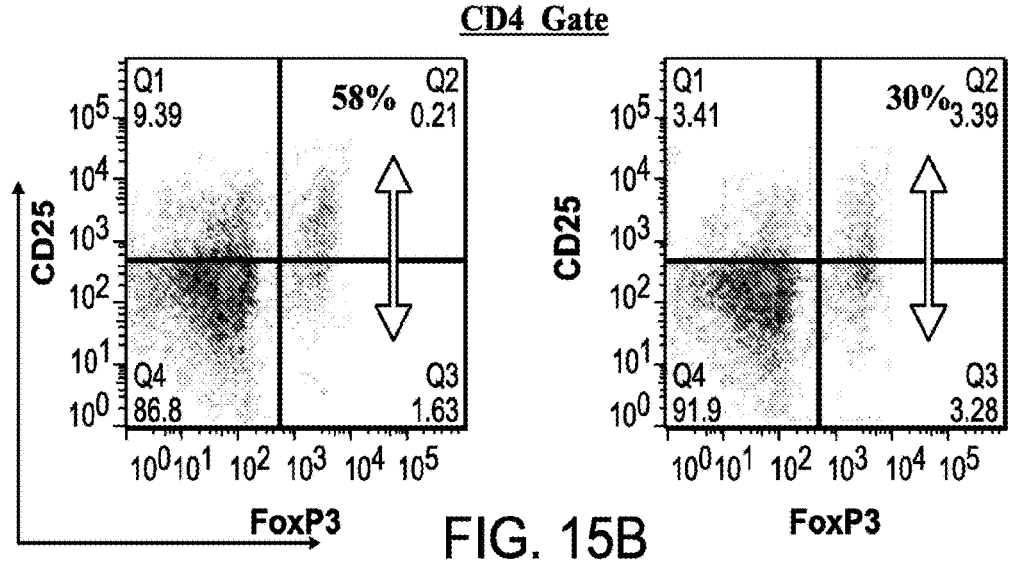
Figure 15C:
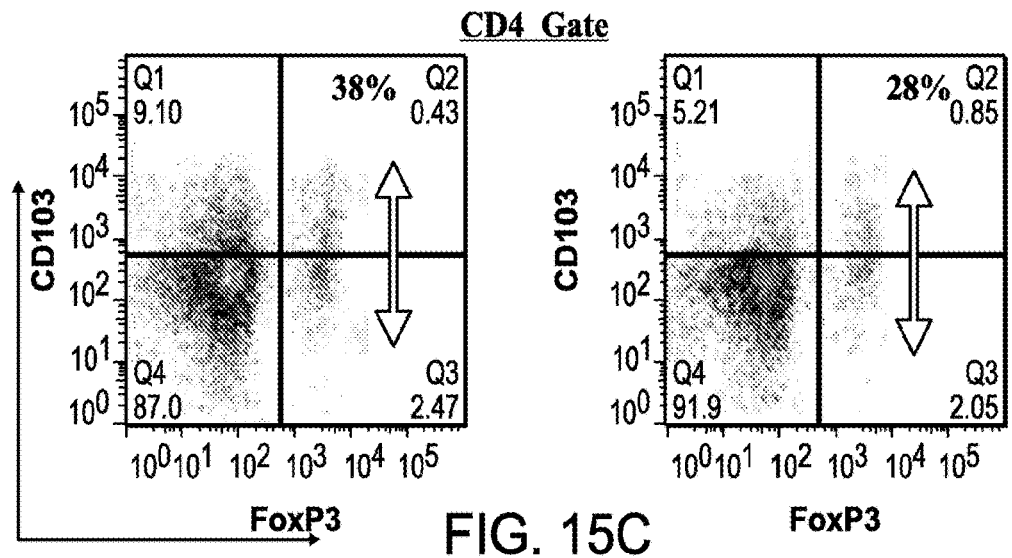

FACS plots of FoxP3 Tregs having a functional phenotype in PSA treated mice are depicted in FIGS. 15A-15C. FIG. 15A shows that cells from the draining cervical lymph nodes (CLN) of PSA (left) or PBS (right) treated HSV infected WT mice treated with ACV from d4 were analyzed at day 6 pi for FoxP3+ CD4 Tregs. FIG. 15B shows that CD4 gated cells in CLN were analyzed for CD25 expressing FoxP3+ Tregs. FIG. 15C shows that CD4 gated cells in CLN were analyzed for CD103+ FoxP3+ Tregs. These results demonstrate that FoxP3 Tregs have a functional phenotype in PSA treated mice.

Line plots showing CD39, CD73 and ICOS surface expression on CD4 and CD8 T cells isolated from mesenteric LN (MLN) of uninfected WT mice at indicated times during oral PSA treatment are depicted in FIGS. 16A-16B. FIG. 16A depicts CD4 T cells isolated from MLN of uninfected WT mice at indicated times during oral PSA treatment. FIG. 16B depicts CD8 T cells isolated from MLN of uninfected WT mice at indicated times during oral PSA treatment. These results demonstrate that PSA increases accumulation of regulatory T cells in mesenteric lymph nodes of wild type mice.

Additional Embodiments

Additional embodiments of the present disclosure are provided below:

A pharmaceutical composition including an effective amount of *Bacteroides fragilis* (*B. fragilis*) capsular polysaccharide A (PSA) and an effective amount of an anti-viral agent.

The composition, where the anti-viral agent is selected from: aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivative thereof, and any combination(s) thereof.

The composition, where the composition is a single-dosage form.

The composition, where composition is a double-dosage form.

The composition, where the double-dosage form includes a first dosage form including the PSA and a second dosage form including the anti-viral agent.

The composition, where the composition is an oral dosage form.

A method of treating a viral infection in a subject in need thereof, the method including administering to the subject an effective amount of *Bacteroides fragilis* (*B. fragilis*) capsular polysaccharide A (PSA).

The method of treating a viral infection in a subject in need thereof, the method including administering to said subject an effective amount of an anti-viral agent.

The of treating a viral infection in a subject in need thereof, where the anti-viral agent is selected from the group consisting of: aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivative thereof, and any combination(s) thereof.

The method of treating a viral infection in a subject in need thereof, where PSA decreases inflammation in said subject.

The method of treating a viral infection in a subject in need thereof, where the viral infection is a DNA or RNA virus infection.

The method of treating a viral infection in a subject in need thereof, where the viral infection is selected from: herpesviruses including herpes simplex virus 1 (HSV-1) infection, HSV-2 infection, varicella-zoster virus (VZV) infection, cytomegalovirus (CMV) infection, Epstein-Barr virus (EBV) infection, Kaposi sarcoma associated herpesvirus (KHSV) infection, Human herpesvirus 6 (HHV6) infection, West-Nile virus infection, polyomaviruses infection, adenovirus infection, respiratory syncytial virus (RSV) infection, norovirus infection, and influenza virus infection.

The method of treating a viral infection in a subject in need thereof, where the inflammation is a neuroinflammation.

The method of treating a viral infection in a subject in need thereof, where the neuroinflammation is due to a neurotropic virus infection.

The method of treating a viral infection in a subject in need thereof, where the virus is an arbovirus, an influenza virus, a herpesvirus, a polyomavirus, or a rotavirus.

The method of treating a viral infection in a subject in need thereof, where the neurotropic virus infection results in neuronal or microglial dysfunction in the CNS of said subject.

The method of treating a viral infection in a subject in need thereof, where the neuroinflammation is HSV encephalitis, autoimmune encephalitis, coxsackievirus encephalitis, echovirus encephalitis, human immunodeficiency virus (HIV) encephalitis, adenovirus encephalitis, Epstein-Barr virus encephalitis, cytomegalovirus encephalitis, lymphocytic choriomeningitis virus (LCMV) encephalitis, arbovirus encephalitis, human herpesvirus 6 encephalitis, rabies virus encephalitis, vaccinia virus encephalitis, measles virus encephalitis, varicella-zoster virus encephalitis, mumps virus encephalitis, or influenza virus encephalitis.

The method of treating a viral infection in a subject in need thereof, where the PSA and said anti-viral agent are administered concurrently or sequentially.

The method of treating a viral infection in a subject in need thereof, where the PSA is administered first, followed by said anti-viral agent.

The method of treating a viral infection in a subject in need thereof, where the PSA is in an oral dosage form.

A method of modulating an immune response in a subject in need thereof, the method including administering to the subject an effective amount of a *Bacteroides fragilis* (*B. fragilis*) capsular polysaccharide A (PSA) and an effective amount of an anti-viral agent.

The method of modulating an immune response in a subject in need thereof, where the method activates B cells.

The method of modulating an immune response in a subject in need thereof, where the method activates T cells.

The method of modulating an immune response in a subject in need thereof, where the method decreases inflammatory monocytes.

The method of modulating an immune response in a subject in need thereof, where the subject has a viral infection selected from: herpesviruses including herpes simplex virus 1 (HSV-1) infection, HSV-2 infection, varicella-zoster virus (VZV) infection, cytomegalovirus (CMV) infection, Epstein-Barr virus (EBV) infection, Kaposi sarcoma associated herpesvirus (KHSV) infection, Human herpesvirus 6 (HHV6) infection, west-nile virus infection, polyomaviruses infection, adenovirus infection, respiratory syncytial virus (RSV) infection, norovirus infection, and influenza virus infection.

The method of modulating an immune response in a subject in need thereof, where the anti-viral agent is selected from: aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivative thereof, and any combination(s) thereof.

The method of modulating an immune response in a subject in need thereof, where the modulating immune response decreases inflammation is said subject.

The method of modulating an immune response in a subject in need thereof, where the subject has a latent viral infection.

The method of modulating an immune response in a subject in need thereof, where the subject has a symptomatic viral infection.

The method of modulating an immune response in a subject in need thereof, where the subject experiences reactivation of a latent viral infection.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of treating a viral infection in a subject in need thereof, the method comprising administering to said subject an effective amount of a zwitterionic polysaccharide, wherein (i) the effective amount is effective to reduce neuroinflammation in the subject, and (ii) the zwitterionic polysaccharide is a zwitterionic bacterial polysaccharide or a zwitterionic capsular polysaccharide.

2. The method of claim 1, wherein said zwitterionic polysaccharide is *Bacteroides fragilis* capsular polysaccharide A.

3. The method of claim 1, wherein said method further comprises administering to said subject an effective amount of an anti-viral agent.

4. The method of claim 3, wherein said anti-viral agent is aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, a pharmaceutically acceptable derivative of any one of the foregoing, or a combination of two or more thereof.

5. The method of claim 1, wherein said viral infection is varicella-zoster virus infection, cytomegalovirus infection, Epstein-Barr virus infection, herpesvirus infection, West-Nile virus infection, polyomavirus infection, adenovirus infection, respiratory syncytial virus infection, norovirus infection, or influenza virus infection.

6. The method of claim 1, wherein the viral infection is a neurotropic virus infection.

7. The method of claim 1, wherein said zwitterionic polysaccharide is in an oral dosage form.

8. A method of modulating an immune response in a subject in need thereof, the method comprising administering to said subject an effective amount of a zwitterionic polysaccharide and an effective amount of an anti-viral agent, wherein:
  (a) the effective amount of the zwitterionic polysaccharide is effective to reduce neuroinflammation in the subject;
  (b) the zwitterionic polysaccharide is a zwitterionic bacterial polysaccharide or a zwitterionic capsular polysaccharide; and
  (c) said subject has a viral infection selected from the group consisting of: varicellazoster virus infection, cytomegalovirus infection, Epstein-Barr virus infection, herpesvirus infection, West-Nile virus infection, polyomavirus infection, adenovirus infection, respiratory syncytial virus infection, norovirus infection, and influenza virus infection.

9. The method of claim 8, wherein said zwitterionic polysaccharide is *Bacteroides fragilis* capsular polysaccharide A.

10. The method of claim 8, wherein said method activates B cells or T cells.

11. The method of claim 8, wherein said method decreases inflammatory monocytes.

12. The method of claim 8, wherein said anti-viral agent is selected from the group consisting of: aciclovir, amantadine, brincidovir, cidofovir, famciclovir, foscarnet, valaciclovir, penciclovir, ganciclovir, valganciclovir, lamivudin, zidovudin, emtricitabin, abacavir, tenofovir, didanosin, stavudin, efavirenz, enfuvirtide, enviroxime, nevirapin, amprenavir, indinavir, saquinavir, ritonavir, lopinavir, atazanavir, nelfinavir, oseltamivir, adefovir, lamivudine, ribavirin, interferon-alpha, pegylated interferon alpha, zanamivir, pharmaceutically acceptable derivative of any one of the foregoing, and a combination of two or more thereof.

* * * * *